United States Patent
Davis et al.

(10) Patent No.: US 10,954,262 B2
(45) Date of Patent: Mar. 23, 2021

(54) TUNICAMYCIN ANALOGUES

(71) Applicant: Oxford University Innovation Limited, Oxford (GB)

(72) Inventors: Benjamin Guy Davis, Oxford (GB); Filip Wyszynski, Oxford (GB); Hua Wang, Oxford (GB)

(73) Assignee: OXFORD UNIVERSITY INNOVATION LIMITED

( * ) Notice: Subject to any disclaimer, the term of this patent is extended or adjusted under 35 U.S.C. 154(b) by 0 days.

(21) Appl. No.: 16/619,504

(22) PCT Filed: Jun. 6, 2018

(86) PCT No.: PCT/GB2018/051539
§ 371 (c)(1),
(2) Date: Dec. 5, 2019

(87) PCT Pub. No.: WO2018/224822
PCT Pub. Date: Dec. 13, 2018

(65) Prior Publication Data
US 2020/0165286 A1 May 28, 2020

(30) Foreign Application Priority Data
Jun. 6, 2017 (GB) ..................................... 1708982

(51) Int. Cl.
| | | |
|---|---|---|
| A01N 43/04 | (2006.01) | |
| A61K 31/70 | (2006.01) | |
| C07H 19/067 | (2006.01) | |
| A61P 31/06 | (2006.01) | |

(52) U.S. Cl.
CPC ............ *C07H 19/067* (2013.01); *A61P 31/06* (2018.01)

(58) Field of Classification Search
None
See application file for complete search history.

(56) References Cited

U.S. PATENT DOCUMENTS

| | | |
|---|---|---|
| 4,237,225 A | 12/1980 | Hamill |
| 4,330,642 A | 5/1982 | Gaul, Jr. et al. |
| 4,336,333 A | 6/1982 | Hamill et al. |

FOREIGN PATENT DOCUMENTS

WO  2012/013960 A2  2/2012

OTHER PUBLICATIONS

Duksin et al. The Journal of Biological Chemistry (1982), vol. 257, pp. 3105-3109.*
International Search Report & Written Opinion for PCT/GB2018/051539, dated Sep. 17, 2018, pp. 1-7.
International Preliminary Report on Patentability for PCT/GB2018/051539, dated Dec. 10, 2019, pp. 1-6.
Takatsuki et al. (1971) J Anibiot. (Tokyo) 24, 215-223, "Isolation and Characterization of Tunicamycin".
Tetsuo et al. (1985) Carbohydrate Research 143, 85-97, "Total Synthesis of Tunicamycin".
Meyers et al. (1993) JACS 115(5) 2036-2038, "A Convergent Synthetic Route to the Tunicamycin Antibiotics Synthesis of ( + )-Tunicamycin V".
"Dissecting Tunicamycinbiosynthesis by genome mining: cloning and heterologous . . . ", F. J. Wyszynski, A.R. Hesketh, M.J. Bibb, B.G. Davis; Chem. Sci., 2010, 1, 581-589.
"Biosynthesis of the tunicamycin antibiotics proceeds via unique exo-glycal intermediates", F. J. Wyszynski, S. Seo Lee, T. Yabe, H. Wang, J.P. Gomez-Escribano, M.J. Bibb, S. Jae Lee, G.J. Davies, B. G. Davis, Nat. Chem. 2012, 4, 539-546.
Andrew G. Myers et al.: "Synthetic Studies of the Tunicamycin Antibiotics. Preparation of (+)-Tunicaminyluracil, (+)-Tunicamycin-V, and 5'-epi-Tunicamycin-V11", Journal of the American Chemical Society, vol. 116, No. 11, Jun. 1, 1994 (Jun. 1, 1994) pp. 4697-4718.

* cited by examiner

*Primary Examiner* — Patrick T Lewis
(74) *Attorney, Agent, or Firm* — Thomas|Horstemeyer, LLP

(57) ABSTRACT

The invention relates to tunicamycin analogues which are compounds according to Formula (I), or pharmaceutically acceptable salts thereof, (I) Wherein [Base] and $R^1$ to $R^9$ are as defined herein. The tunicamycin analogues are useful in the prevention or treatment of bacterial infection, in particular of tuberculosis.

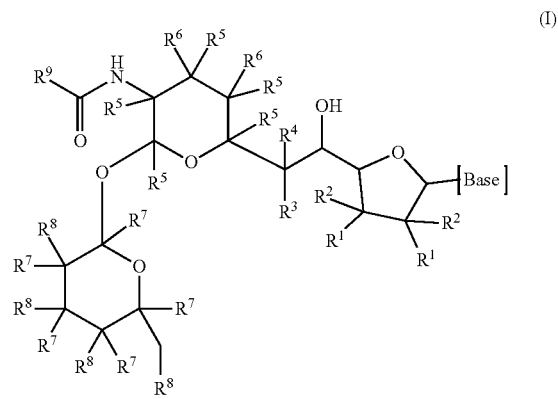

20 Claims, 5 Drawing Sheets

Fig. 4
Tunicamycin (TM)
Di-N-octanoyl (diOct) TM (E3)
Di-N-nonanoyl (diNon) TM (E4)
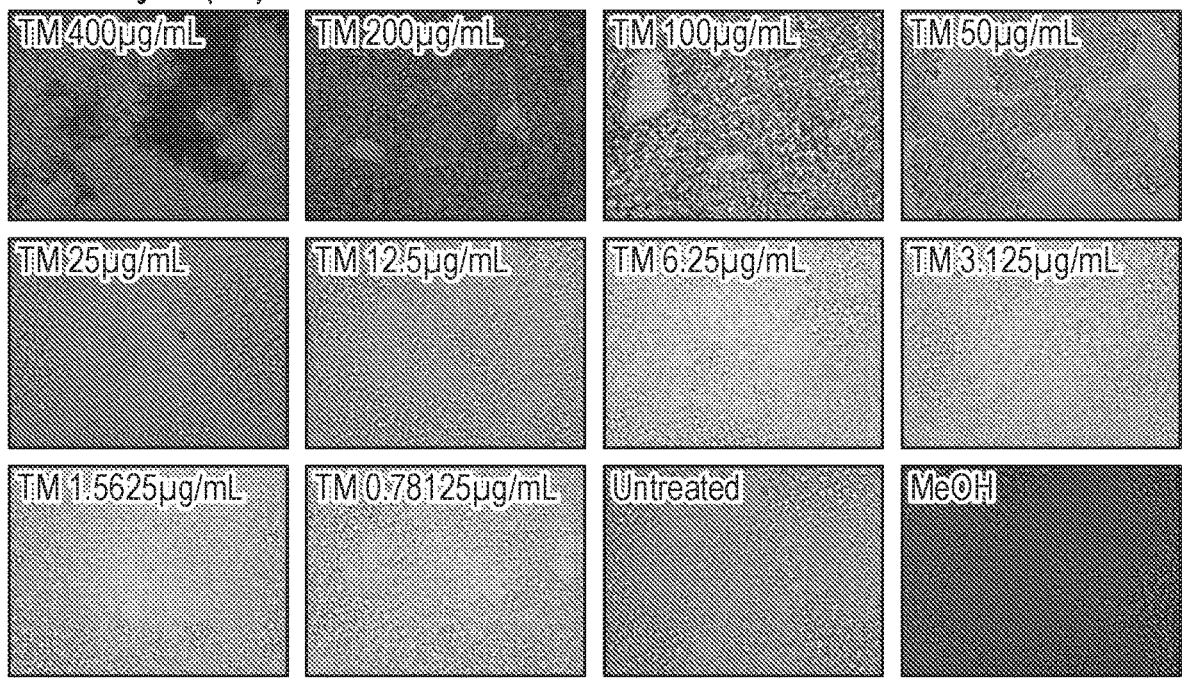
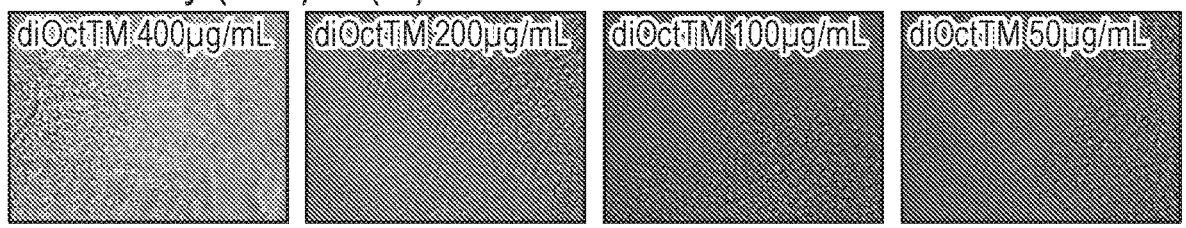
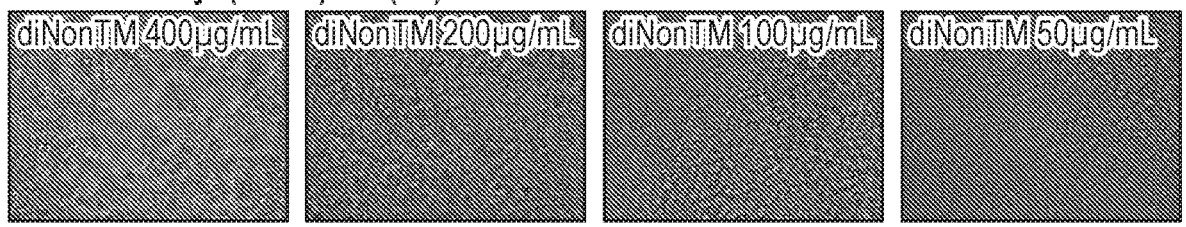

TUNICAMYCIN ANALOGUES

CROSS-REFERENCE TO RELATED APPLICATIONS

This application is the National Stage of International Application No. PCT/GB2018/051539, filed Jun. 6, 2018, which claims priority to GB 1708982.2, filed Jun. 6, 2017, which are entirely incorporated herein by reference.

FIELD OF THE INVENTION

The present invention relates to a series of lipid-altered tunicamycin analogues which are useful as antibacterial agents. The invention also relates to the use of lipid-altered tunicamycin analogues as antibacterial agents and to the provision of pharmaceutical compositions comprising lipid-altered tunicamycins.

BACKGROUND

Antibiotics with broad activity yet unique modes of action are desirable for tackling pathogenic infections. However, the current range of effective antibiotics is shrinking as pathogens acquire immunity towards commonly prescribed antibiotics. There is therefore a need to provide new antibiotics with broad activity against pathogens.

Tunicamycin is a widely known and naturally occurring nucleoside antibiotic that has been demonstrated to exhibit antibacterial activity. The antibacterial properties of tunicamycin derive from the transfer of a bacterially unique sugar-1-phosphoryl unit onto a bacteria specific lipid, catalysed by the transmembrane enzyme MraY translocase. MraY catalyses the formation of the key peptidoglycan precursor undecaprenyl-pyrophosphoryl-N-acetylmuramoyl pentapeptide, a key peptidoglycan precursor. MraY exists in both gram-positive and gram-negative bacteria. However, there are currently no clinically approved antibiotics which target MraY.

Although tunicamycin is a potent, naturally-occurring nucleoside antibiotic, it is also highly toxic towards eukaryotic cells. For this reason, the clinical use of tunicamycin in the treatment of or prophylaxis against bacterial infection is not feasible. The toxicity of tunicamycin arises from its ability to inhibit both N-glycosylation and N-acylation of eukaryotic proteins. For instance, it is believed that specific binding to the active site of UDP-GlcNAc:dolichyl phosphate GlcNAc-1-phosphate transferase (GTP) blocks production of the lipid-linked precursor dolichyl-pyrophosphory-N-acetyl-glucosamine (Dol-PP-GlcNAc) and terminates asparagine-linked glycoprotein synthesis at the first committed step. This property has, however, made tunicamycin a valuable biochemical tool in glycobiology to study post-translational modification of eukaryotic proteins.

Tunicamycin as a natural product is a mixture of homologous secondary metabolites (see structure below), produced by several *Streptomyces* species, and belongs to the same family of nucleoside secondary metabolites as streptovirudin and corynetoxin. The components within the naturally occurring tunicamycin mixture differ in the length of the lipid chains on the tunicamine core, but the separation of these homologues is a difficult and tedious process. Early studies revealed that factors including the length of the lipid chain on the tunicamine core, the degree of saturation and the particular isomer all interplayed in determining the bioactivity of the relevant homologue in prokaryotes and eukaryotes. As different homologues cannot be easily isolated, almost all studies in the literature use tunicamycin as a mixture.

Natural Tunicamycin:

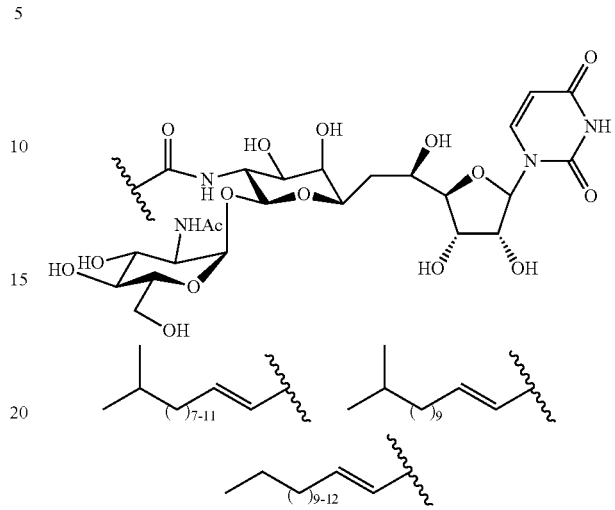

SUMMARY OF THE INVENTION

The inventors have surprisingly found that it is possible to create analogues of tunicamycin in which the antibacterial activity is separated from the mammalian toxicity. In particular, the inventors have found that by modifying the sugar attached to the tunicamine core to incorporate a lipid, 'lipid-altered' tunicamycin analogues displaying enhanced potency against pathogenic and non-pathogenic bacteria, yet minimal cytotoxicity towards mammalian cells, can be obtained.

Accordingly, the invention provides an oligosaccharide which is a compound according to Formula (I), or a pharmaceutically acceptable salt thereof,

[FORMULA (I)]

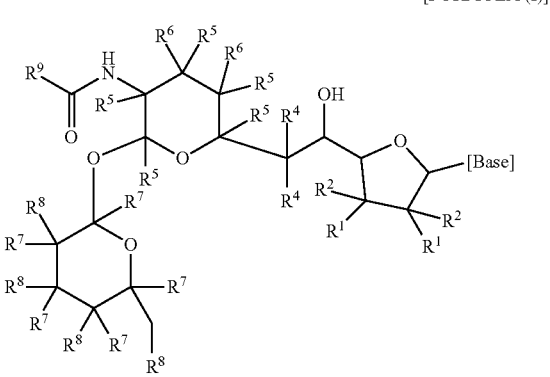

wherein:
  [Base] is a natural nucleobase selected from adenine, cytosine, guanine, thymine and uracil;
  each $R^1$, which may be the same or different, is independently H, OH, —OPO(OH)$_2$, or halogen;
  each $R^2$, which may be the same or different, is independently H, halogen, or $C_1$ to $C_2$ alkyl;
  $R^3$ and $R^4$, which may be the same or different, are each independently H, OH, halogen, $C_1$ to $C_2$ alkyl, $C_1$ to $C_2$ alkoxy, or —NR$^{10}$R$^{11}$;

each $R^5$, which may be the same or different, is independently H, halogen, or $C_1$ to $C_2$ alkyl;

each $R^6$, which may be the same or different, is independently OH, halogen, —OPO(OH)$_2$, —OCO$_2$CH$_3$, —NHCOCH$_3$ or $C_1$ to $C_2$ alkoxy;

one or more $R^7$ and/or one or more $R^8$ is a group —NHC(O)R$^9$; the remaining groups $R^7$, which may be the same or different, are independently H, halogen, or $C_1$ to $C_2$ alkyl; and the remaining groups $R^8$, which may be the same or different, are independently OH, halogen, —OPO(OH)$_2$, or —OCO$_2$CH$_3$, —NHCOCH$_3$ or $C_1$ to $C_2$ alkoxy;

each $R^9$, which may be the same or different, is independently $C_3$ to $C_{20}$ alkyl, $C_3$ to $C_{20}$ alkenyl, or $C_3$ to $C_{20}$ alkynyl, wherein $R^9$ may be unsubstituted or may be substituted by from 1 to 6 substituents selected from halogen, OH, $C_1$ to $C_4$ alkoxy and —NR$^{10}$R$^{11}$; and each $R^{10}$ and $R^{11}$, which may be the same or different, is independently H or $C_1$ to $C_4$ alkyl.

The invention also provides a pharmaceutical composition comprising an oligosaccharide as described herein, and a pharmaceutically acceptable carrier or diluent.

The invention also provides an oligosaccharide as described herein, or a pharmaceutical composition as described herein, for use in treating or preventing bacterial infection in a subject.

BRIEF DESCRIPTION OF THE FIGURES

FIG. 4 shows the results of cell morphology tests, including cell images of HEK293 cells in the presence of TM and two compounds of the invention over two fold dilutions.

FIG. 6(*a*) contains the TOF-MS for crude tunicamycin extracted from an *S. chartreusis* NRRL 3882 culture, while FIG. 6(*b*) contains the TOF-MS for a commercial tunicamycin standard obtained from Sigma Aldrich.

DETAILED DESCRIPTION OF THE INVENTION

Figure 1:
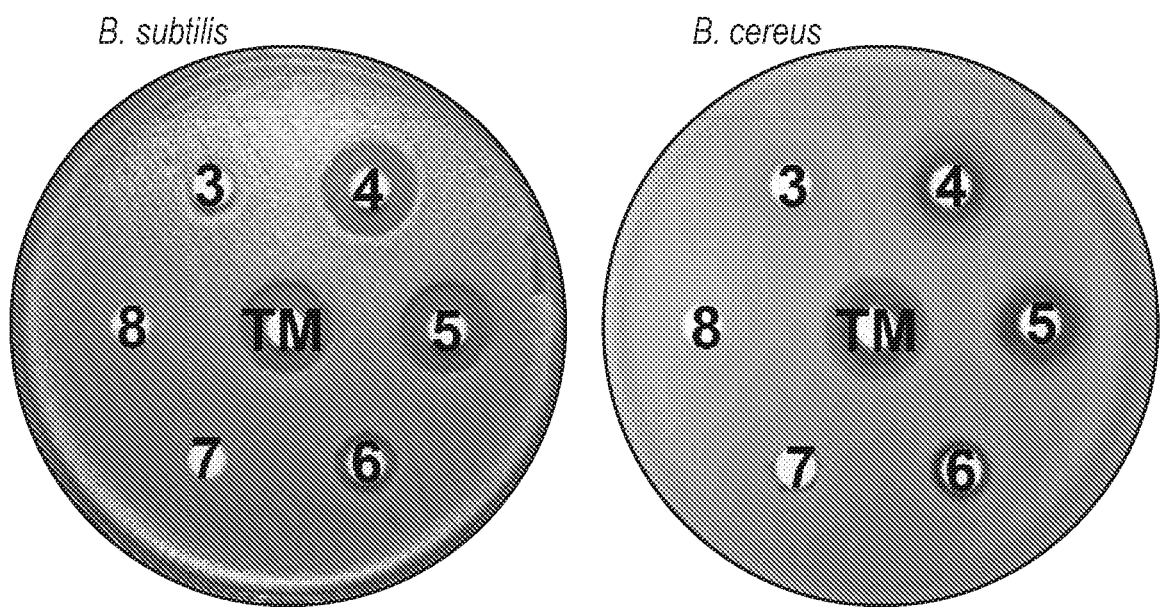
FIG. 1 shows results of the Kirby-Bauer disc diffusion susceptibility test conducted using *Bacillus subtilis* and *Bacillus cereus* as test organisms using compounds according to the invention and natural tunicamycin.
Figure 2:
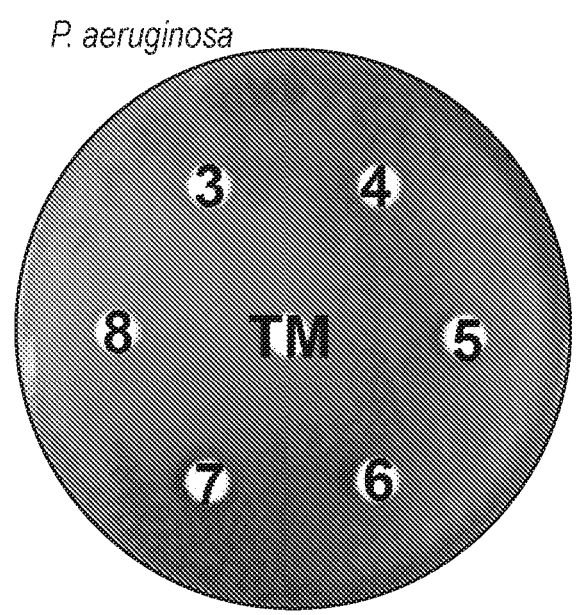
FIG. 2 shows corresponding results for the organism *Pseudomonas aeruginosa*.
Figure 3:
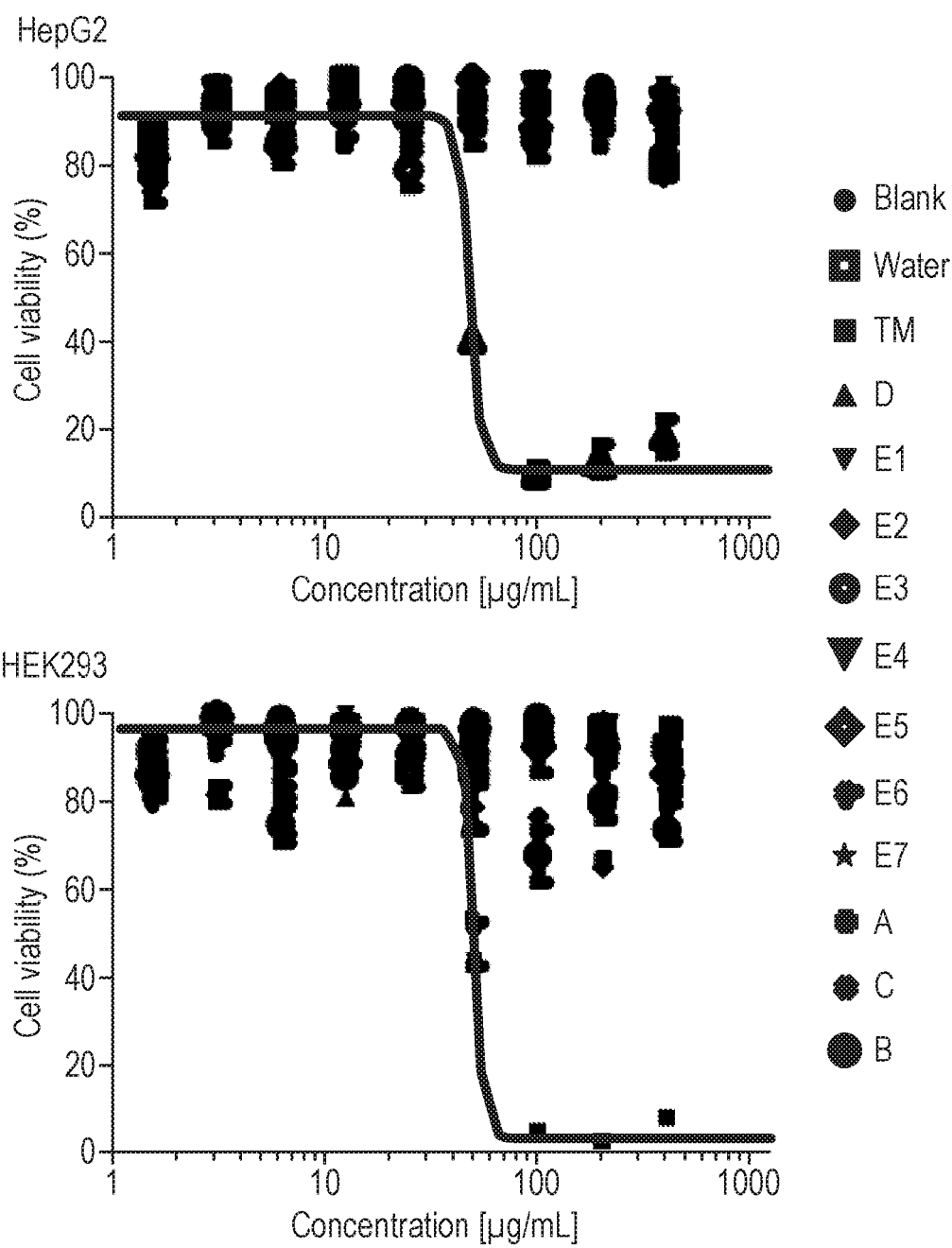
FIG. 3 shows dose response curves from HepG2 and HEK293 cell proliferation tests for TM.

As used herein, a $C_3$ to $C_{20}$ alkyl group is a linear or branched alkyl group containing from 3 to 20 carbon atoms. Typically a $C_3$ to $C_{20}$ alkyl group is a $C_4$ to $C_{16}$ alkyl group, e.g. a $C_6$ to $C_{12}$ alkyl group. A $C_6$ to $C_{12}$ alkyl group is a linear or branched alkyl group containing from 6 to 12 carbon atoms. Examples of $C_6$ to $C_{12}$ alkyl groups include groups —(CH$_2$)$_n$CH$_3$ wherein n is from 5 to 11, and branched alkyl groups including, methyl-pentyl, methyl-hexyl and dimethyl-hexyl such as 2,6-dimethylhexyl. A $C_1$ to $C_4$ alkyl group is a linear or branched alkyl group containing from 1 to 4 carbon atoms, for example, methyl, ethyl, n-propyl, iso-propyl, n-butyl, sec-butyl or tert-butyl. A $C_1$ to $C_4$ alkyl group is typically a $C_1$ to $C_2$ alkyl group. A $C_1$ to $C_2$ alkyl group is methyl or ethyl, typically methyl. For the avoidance of doubt, where two alkyl groups are present, the alkyl groups may be the same or different.

As used herein, a $C_3$ to $C_{20}$ alkenyl group is a linear or branched alkenyl group containing from 3 to 20 carbon atoms and having one or more, e.g. one or two, double bonds. Typically a $C_3$ to $C_{20}$ alkenyl group is a $C_4$ to $C_{16}$ alkenyl group, e.g. a $C_6$ to $C_{12}$ alkenyl group. A $C_6$ to $C_{12}$ alkenyl group is a linear or branched alkenyl group containing from 6 to 12 carbon atoms and having one or more, e.g. one or two, double bonds. Examples of $C_6$ to $C_{12}$ alkenyl groups include hexenyl, heptenyl, octenyl, decenyl and undecenyl, methyl-hexenyl and dimethyl-hexenyl. For the avoidance of doubt, where two alkenyl groups are present, the alkenyl groups may be the same or different.

As used herein, a $C_3$ to $C_{20}$ alkynyl group is a linear or branched alkynyl group containing from 3 to 20 carbon atoms and having one or more, e.g. one or two, triple bonds. Typically a $C_3$ to $C_{20}$ alkynyl group is a $C_4$ to $C_{16}$ alkynyl group, e.g. a $C_6$ to $C_{12}$ alkynyl group. A $C_6$ to $C_{12}$ alkynyl group is a linear or branched alkynyl group containing from 6 to 12 carbon atoms and having one or more, e.g. one or two, double bonds. Examples of $C_6$ to $C_{12}$ alkynyl groups include hexynyl, heptynyl, octynyl, decynyl and undecynyl, methyl-hexynyl and dimethyl-hexynyl. For the avoidance of doubt, where two alkynyl groups are present, the alkynyl groups may be the same or different.

An alkyl, alkenyl or alkynyl group as used herein may be unsubstituted or substituted. Substituted alkyl, alkenyl or alkynyl groups typically carry from one to six, e.g. one, two or three, e.g. one substituent selected from halogen, OH, $C_1$ to $C_4$ alkoxy and —NR$^{10}$R$^{11}$.

As used herein, a halogen is typically chlorine, fluorine, bromine or iodine and is preferably chlorine, bromine or fluorine.

As used herein, a $C_1$ to $C_4$ alkoxy group is typically a said $C_1$ to $C_4$ alkyl group attached to an oxygen atom. A $C_1$ to $C_2$ alkoxy group is methoxyl or ethoxy.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Lipid Altered Tunicamycin Analogues

The lipid altered tunicamycin analogues of the present invention are an oligosaccharide which is a compound according to Formula (I), or a pharmaceutically acceptable salt thereof,

[FORMULA (I)]

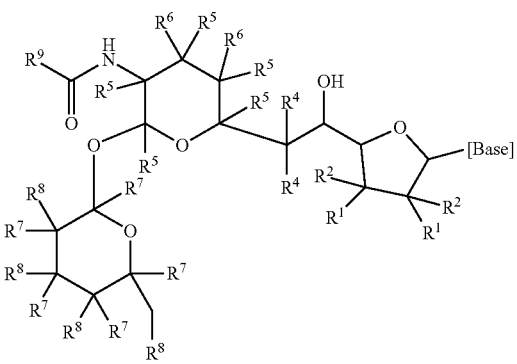

In Formula (I), the stereochemistry is not limited. However, preferred oligosaccharides of Formula (I) have a structure according to Formula (II).

[FORMULA (II)]

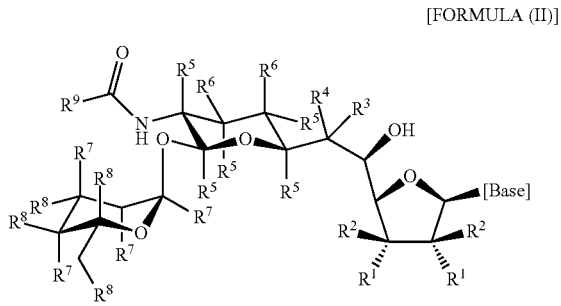

Compounds of formula (I) containing one or more chiral centre may be used in enantiomerically or diastereoisomerically pure form, or in the form of a mixture of isomers. Further, for the avoidance of doubt, the compounds of the invention may be used in any tautomeric form. Preferably, the compounds of formula (I) are those according to Formula (II), i.e. the compounds of formula (I) preferably have the stereochemistry as shown in Formula (II). Typically, the oligosaccharide described herein contains at least 50%, preferably at least 60, 75%, 90% or 95% of the compound having the stereochemistry of Formula (II). More preferably, the oligosaccharide described herein contains at least 98%, 99% or 99.5% of the compound having the stereochemistry of Formula (II). Thus, the compounds is preferably substantially optically pure.

In Formula (I), [Base] is a natural nucleobase selected from adenine, cytosine, guanine, thymine and uracil. Preferably, [Base] is a pyrimidine nucleobase. More preferably, the base is thymine (T) or uracil (U), with uracil (U) being most preferable.

In Formula (I), each $R^1$, which may be the same or different, is typically OH or —OPO(OH)$_2$, preferably each $R^1$ is OH.

In Formula (I), each $R^2$, which may be the same or different, is typically H or methyl, preferably each $R^2$ is H.

In Formula (I), $R^3$ and $R^4$, which may be the same or different, are typically H, OH, methyl, NH$_2$ or halogen, with H and OH being preferable. More preferably $R^3$ and $R^4$ are both H.

In Formula (I), each $R^5$, which may be the same or different, is typically H or $C_1$ to $C_2$ alkyl, preferably each $R^5$ is H.

In Formula (I), each $R^6$, which may be the same or different, is typically OH, —NHCOCH$_3$ or —OPO(OH)$_2$. Each $R^6$ is preferably OH.

In Formula (I), one or more $R^7$ and/or one or more $R^8$ is a group —NHC(O)$R^9$; the remaining groups $R^7$, which may be the same or different, are independently H, halogen, or $C_1$ to $C_2$ alkyl; and the remaining groups $R^8$, which may be the same or different, are independently OH, halogen, —OPO(OH)$_2$, —OCO$_2$CH$_3$, —NHCOCH$_3$ or $C_1$ to $C_2$ alkoxy. Each remaining group $R^7$ is preferably H or $C_1$ to $C_2$ alkyl, with H being most preferable. Each remaining group $R^8$ is preferably OH, —NHCOCH$_3$ or —OPO(OH)$_2$, with OH being most preferable.

Each $R^{10}$ and $R^{11}$, which may be the same or different, is typically H or $C_1$ to $C_2$ alkyl. Preferably, $R^{10}$ and $R^{11}$ are H.

Typically, each $R^9$ group is the same.

Typically, each $R^9$ is $C_3$ to $C_{20}$ alkyl or $C_3$ to $C_{20}$ alkenyl. Alkyl groups, in particular n-alkyl groups, are preferred in one embodiment. Thus, $R^9$ is a carbon chain of at least 3 carbon atoms. Preferably, $R^9$ has at least 4 carbon atoms, more preferably at least 6 carbon atoms, still more preferably at least 7 carbon atoms. $R^9$ is a carbon chain of no more than 20 carbon atoms, preferably no more than 16, more preferably no more than 12, still more preferably no more than 9 carbon atoms. $R^9$ may therefore be an alkyl, alkenyl or alkynyl group, preferably an alkyl or alkenyl group, having from, for example, 3 to 20 carbon atoms, 4 to 16 carbon atoms, 6 to 12 carbon atoms, or 7 to 9 carbon atoms, such as 8 carbon atoms. $R^9$ is preferably unsubstituted or is substituted by from 1 to 4 substituents, e.g. from 1 to 3 substituents such as one or two substituents. The substituents are preferably selected from halogen, OH, $C_1$ to $C_4$ alkoxy, and —NR$^{10}$R$^{11}$. More preferably, the substituents are selected from halogen, OH and $C_1$ to $C_2$ alkoxy. Still more preferably, the substituents are selected from halogen and OH. Most preferably, $R^9$ is unsubstituted.

In Formula (I), it is preferable that one of the $R^7$ and/or $R^8$ groups which are —NHC(O)$R^9$ is bonded to the C2" carbon (see Formula (IV) below). The C2" carbon is the carbon atom adjacent to the C1" carbon atom. The C1" carbon atom is connected via oxygen to the sugar ring carrying $R^5$ and $R^6$ groups.

In Formula (I), it is preferable that the total number of $R^7$ and $R^8$ groups which are —NHC(O)$R^9$ is from 1 to 3. Preferably, the total number of $R^7$ and $R^8$ groups which are —NHC(O)$R^9$ is 1 or 2, and most preferably 1.

When one group $R^8$ is —NHC(O)$R^9$ it is preferable that the ring carrying groups $R^7$ and $R^8$ has a structure according to Formula (IV):

[FORMULA (IV)]

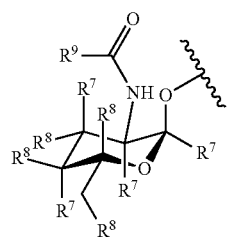

A preferred lipid altered tunicamycin analogue of the present invention is an oligosaccharide which is a compound according to Formula (I) or (II) above, or a pharmaceutically acceptable salt thereof, wherein:

[Base] is thymine (T) or uracil (U);

each $R^1$, which may be the same or different, is OH or —OPO(OH)$_2$;

each $R^2$, which may be the same or different, is H or methyl;

$R^3$ and $R^4$, which may be the same or different, are H, OH, methyl, NH$_2$ or halogen;

each $R^5$, which may be the same or different, is H or $C_1$ to $C_2$ alkyl;

each $R^6$, which may be the same or different, is OH, —NHCOCH$_3$ or —OPO(OH)$_2$;

one, two or three groups, preferably one group, selected from the groups $R^7$ and $R^8$ is a group —NHC(O)R$^9$; the remaining groups $R^7$, which may be the same or different, are independently H or $C_1$ to $C_2$ alkyl; and the remaining groups $R^8$ which may be the same or different, are independently OH, —NHCOCH$_3$ or —OPO(OH)$_2$;

each $R^9$ is the same or different and is, independently, $C_4$ to $C_{16}$ alkyl or $C_4$ to $C_{16}$ alkenyl group which is unsubstituted or is substituted by from 1 to 4 substituents selected from halogen, OH, $C_1$ to $C_4$ alkoxy, and —NR$^{10}$R$^{11}$; and each $R^{10}$ and $R^{11}$, which may be the same or different, is H or $C_1$ to $C_2$ alkyl.

A more preferred lipid altered tunicamycin analogue of the present invention is an oligosaccharide which is a compound according to Formula (III), or a pharmaceutically acceptable salt thereof,

[FORMULA (III)]

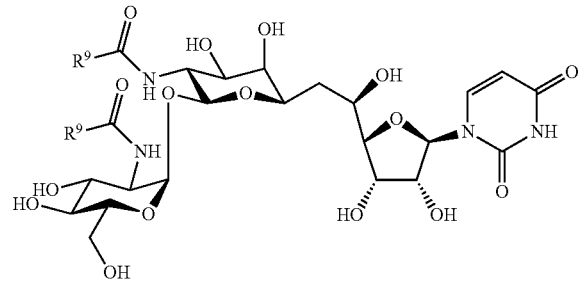

wherein each $R^9$, which may be the same or different, is defined as above. Preferably each $R^9$ is the same. Preferably, in this embodiment, each $R^9$ is $C_6$ to $C_{12}$ alkyl or $C_6$ to $C_{12}$ alkenyl, in particular $C_6$ to $C_{12}$ alkyl, preferably linear $C_6$ to $C_{12}$ alkyl. In one embodiment $R^9$ is a linear $C_7$ to $C_9$ alkyl group. Typically, $R^9$ is unsubstituted or is substituted by one or two substituents selected from halogen and OH. Most preferably, $R^9$ is unsubstituted.

A particularly preferred lipid altered tunicamycin analogue of the present invention is an oligosaccharide which is a compound according to Formula (III), or a pharmaceutically acceptable salt thereof, wherein $R^9$ is selected from

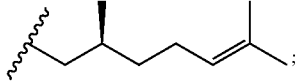
E1

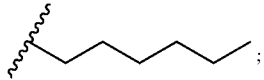
E2

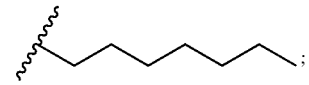
E3

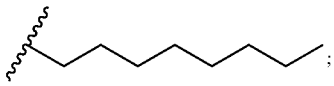
E4

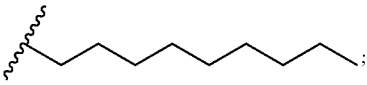
E5

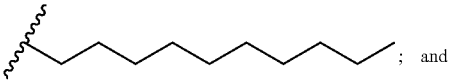
E6; and

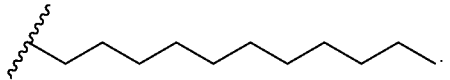
E7

The compounds of the invention can, for example, be prepared according to the following general reaction sequence. A tunicamyl derivative may be derived from crude tunicamycin. Standard modifications can be employed to alter the structure of the tunicamyl derivative at this or subsequent stages in the synthesis. Derivatives may be produced by introduction of, for example, BOC (tert-butyloxycarbonyl) groups followed by base treatment. Acylation may also be used. Divergent intermediates containing the fully intact tunicamycin-derived core scaffold may be derived by the further introduction of BOC groups followed by mild basic cleavage. Lipids may be introduced to yield lipid-modified tunicamycin analogues.

The compounds of the present invention are therapeutically useful. The present invention therefore provides a lipid altered tunicamycin analogue of the formula (I), as defined above, or a pharmaceutically acceptable salt thereof, for use in treating the human or animal body. For the avoidance of doubt, the compounds of formula (I) can, if desired, be used in the form of solvates.

Also provided is a pharmaceutical composition comprising lipid altered tunicamycin analogue of the formula (I), as defined above, or a pharmaceutically acceptable salt thereof, and a pharmaceutically acceptable carrier or diluent. Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer.

As explained above, the compounds of the invention are useful in treating or preventing a bacterial infection. The present invention therefore provides a lipid altered tunicamycin analogue of the formula (I), as defined above, or a pharmaceutically acceptable salt thereof, for use in treating or preventing a bacterial infection. Also provided is a method for treating a subject suffering from or susceptible to a bacterial infection, which method comprises administering to said subject an effective amount of a lipid altered tunicamycin analogue of the formula (I), as defined above, or a pharmaceutically acceptable salt thereof. Further provided is the use of a lipid altered tunicamycin analogue of the formula (I), as defined above, or a pharmaceutically acceptable salt thereof, in the manufacture of a medicament for use in treating or preventing a bacterial infection.

In one aspect, the subject is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of being infected by a bacterium.

The bacterium causing the infection may be any bacterium expressing MraY or an analogue thereof. Typically the bacterium causing the infection expresses MraY. The bacterium may, for instance, be any bacterium that has a peptidoglycan component in the cell wall. The bacterium may be Gram-positive or Gram-negative. In a preferred instance the bacterium is Gram-positive. The bacterium may in particular be a pathogenic bacterium.

In one preferred instance, the bacterium may be one selected from a bacterium of the following Gram-positive bacteria families: *Actinomyces, Bacillus* (including *Enterococcus*), *Clostridium, Corynebacterium, Listeria, Mycobacterium, Mycoplasma, Streptococcus* and *Staphylococcus* (including MRSA). Examples of Gram-positive bacteria include *Actinomyces israelii, Clostridium botulinum, Clostridium difficile, Clostridium perfringens, Clostridium tetani, Corynebacterium diptheriae, Enterococcus faecalis, Enterococcus faecium, Listeria monocytogenes, Mycobacterium avium, Mycobacterium tuberculosis, Mycobacterium leprae, Mycoplasma pneumoniae, Staphylococcus aureus, Staphylococcus epidermidis, Staphylococcus saprophyticus, Streptococcus agalactiae, Streptococcus pneumoniae* and *Streptococcus pyogenes*.

In one preferred instance, the bacterium may be one selected from a bacterium of the following Gram-negative bacteria families: *Acinetobacter, Bordetella, Borrelia, Brucella, Burkholderia, Campylobacter, Chlamydia, Chlamydophila, Enterobacter, Escherichia, Helicobacter, Hemophilus, Klebsiella, Legionella, Leptospira, Moraxella, Neisseria, Proteus, Pseudomonas, Salmonella, Serratia, Shigella, Treponema, Vibrio* and *Yersinia*. Examples of Gram-negative bacteria include *Acinetobacter baumannii, Bordetella pertussis, Borrelia burgdorferi, Brucella abortus, Brucella canis, Brucella melitensis, Brucella suis, Burkholderia cenocepacia, Campylobacter jejuni, Chlamydia pneumoniae, Chlamydia psittaci, Chlamydia trachomatis, Enterobacter cloacae, Escherichia coli, Francisella tularensis, Haemophilus influenzae, Helicobacter pylori, Klebsiella pneumoniae, Legionella pneumophila, Leptospira interrogans, Moraxella catarrhalis, Neisseria gonorrhoeae, Neisseria meningitidis, Proteus mirabilis, Pseudomonas aeruginosa, Rickettsia rickettsii, Salmonella enteritidis, Salmonella typhi, Salmonella typhimurium, Serratia marcescens, Shigella sonnei, Treponema pallidum, Vibrio cholerae* and *Yersinia pestis*.

In a preferred embodiment, the bacterium is a *Bacillus, Pseudomonas,* or *Mycobacterium*. In another instance, the bacterium is a *Streptococcus* or *Pseudomonas*, particularly where the condition to be treated is pneumonia. In another instance the bacterium may be *Shigella, Campylobacter* or *Salmonella*, particularly where the condition to be treated is a food borne infection. Alternatively, the condition to be treated may be tetanus, typhoid fever, diphtheria, syphilis or leprosy. For instance, the bacterium may be one selected from the group *Clostridium tetani, Salmonella typhi, Corynebacterium diptheriae, Treponema pallidum* and *Mycobacterium leprae*. In another instance, the bacterium may be an opportunistic pathogen, and in a preferred instance may be selected from *Pseudomonas aeruginosa, Burkholderia cenocepacia,* and *Mycobacterium avium*. In a further instance, the bacterium may be *Chlamydia, Mycobacterium* or *Brucella*. In a further preferred instance, the bacterium is a *Mycobacterium* (including tuberculosis and leprae). In one instance the bacterium is *Mycobacterium tuberculosis*, particularly where the condition to be treated or prevented is tuberculosis. In further instances, the bacterium may be *Chlamydia pneumoniae, Chlamydia trachomatis, Chlamydophila psittaci, Mycobacterium leprae, Mycobacterium tuberculosis* or *Mycoplasma pneumoniae*.

The invention may be used to treat or prevent infections and conditions caused by any of the above-mentioned bacteria. In particular, the oligosaccharides described herein may be used in the treatment or prevention of pneumonia, food borne infections, tetanus, typhoid fever, diphtheria, syphilis, leprosy or tuberculosis. In particular, the oligosaccharides described herein may be used in the treatment or prevention of tuberculosis.

The lipid altered tunicamycin analogue or a pharmaceutically acceptable salt thereof can be administered to the subject in order to prevent the onset of one or more symptoms of the bacterial infection. This is prophylaxis. In this embodiment, the subject can be asymptomatic. The subject is typically one that has been exposed to the bacterium. A prophylactically effective amount of the lipid altered tunicamycin analogue is administered to such a subject. A prophylactically effective amount is an amount which prevents the onset of one or more symptoms of the bacterial infection.

The lipid altered tunicamycin analogue or a pharmaceutically acceptable salt thereof can be administered to the subject in order to treat one or more symptoms of the bacterial infection. In this embodiment, the subject is typically symptomatic. A therapeutically effective amount of the lipid altered tunicamycin analogue is administered to such a subject. A therapeutically effective amount is an amount effective to ameliorate one or more symptoms of the disorder.

The lipid altered tunicamycin analogue or a pharmaceutically acceptable salt thereof may be administered in a variety of dosage forms. Thus, it can be administered orally, for example as tablets, troches, lozenges, aqueous or oily suspensions, dispersible powders or granules. The lipid altered tunicamycin analogue or a pharmaceutically acceptable salt thereof may also be administered parenterally, whether subcutaneously, intravenously, intramuscularly, intrasternally, transdermally or by infusion techniques. The lipid altered tunicamycin analogue or a pharmaceutically acceptable salt thereof may also be administered as a suppository.

The lipid altered tunicamycin analogue or a pharmaceutically acceptable salt thereof is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions. Pharmaceutical compositions suitable for delivery by needleless injection, for example, transdermally, may also be used.

In some embodiments, the invention provides an injectable composition comprising the lipid altered tunicamycin analogue or a pharmaceutically acceptable salt thereof.

In one embodiment, the invention provides an injectable composition comprising the lipid altered tunicamycin analogue or a pharmaceutically acceptable salt thereof, a buffer solution, an alcohol and optionally a surfactant. In this embodiment, the lipid altered tunicamycin analogue or pharmaceutically acceptable salt thereof is typically present in an amount of up to 5 mg/mL, for example from 0.001 to 4 mg/mL, e.g. 0.5 to 3 mg/mL. The buffer solution typically has a pH of approximately 7, such as from pH 6 to pH 8.5, preferably from pH 7 to pH 7.5. The buffer solution may be a phosphate buffer saline solution (PBS). The buffer solution usually forms the basis of the injectable composition. The amount of buffer solution is typically at least 50% of the solution by weight, for instance from 50% to 99.5%, e.g. from 70% to 95% by weight. The alcohol in the injectable composition is usually a $C_{1-6}$ alcohol such as methanol, ethanol or propanol. Preferably the alcohol is ethanol. The amount of alcohol in the injectable composition is usually less than 50% by weight, for example from 0.5% to 50%, e.g. from 5% to 30% by weight. Where the surfactant is present, the surfactant may be present in an amount of from 0.1% to 10% by weight, e.g. from 0.5% to 5% by weight. The surfactant may be, for example, Tween-80.

A therapeutically or prophylactically effective amount of the lipid altered tunicamycin analogue or a pharmaceutically acceptable salt thereof is administered to a subject. The dose may be determined according to various parameters, especially according to the compound used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The invention provides a pharmaceutical composition comprising a lipid altered tunicamycin analogue of the invention or a pharmaceutically acceptable salt thereof and a pharmaceutically acceptable carrier. Such pharmaceutical compositions comprise a therapeutically or prophylactically effective amount of the lipid altered tunicamycin analogue or a pharmaceutically acceptable salt thereof and may further comprise instructions to enable the kit to be used in the methods described herein or details regarding which subjects the method may be used for.

The following Examples illustrate the invention. They do not however, limit the invention in any way. In this regard, it is important to understand that the particular assay used in the Examples section is designed only to provide an indication of antibacterial activity. There are many assays available to determine such activity, and a negative result in any one particular assay is therefore not determinative.

EXAMPLES

Abbreviations

ACN acetonitrile
$Ac_2O$ acetic anhydride
CFU colony forming unit
CLSI Clinical and Laboratory Standards Institute
DCM dichloromethane
DIC N,N'-diisopropylcarbodiimide
DMAP 4-dimethylaminopyridine
DMEM Dulbecco's modified Eagle's medium
DMF dimethylformamide
DSMZ Deutsche Sammlung von Mikroorganismen and Zellkulturen GmbH
EtOAc ethyl acetate
FA formaldehyde
FBS fetal bovine serum
HPLC high performance liquid chromatography
HRMS high resolution mass spectroscopy
IC50 half maximal inhibitory concentration
iPOH/iPrOH isopropanol
IR infra-red (spectroscopy)
LRMS low resolution mass spectroscopy
MBC minimum bactericidal concentration
MH Mueller-Hinton
MIC minimum inhibitory concentration
Mp melting point
MraY phospho-N-acetylmuramoyl-pentapeptide transferase
NIH National Institute of Health
NMR nuclear magnetic resonance
$OD_{600}$ optical density at a wavelength of 600 nm
PBS phosphate buffered saline
$R_f$ retardation factor
RT room temperature
RTI relative therapeutic index
SEM standard error of the mean
TEA triethyl amine
TFA trifluoroacetic acid
THF tetrahydrofuran
TLC thin layer chromatography
TM Tunicamycin
W water General Considerations Proton ($^1H$) nuclear magnetic resonance (NMR) (δH) spectra were recorded on Bruker DPX 200 (200 MHz), Bruker DPX 400 (400 MHz), Bruker DQX 400 (400 MHz), or Bruker AVC 500 (500 MHz) spectrometer. Carbon ($^{13}C$) nuclear magnetic resonance spectra were recorded on Bruker DQX400 (100 MHz) or Bruker AVC 500 (125 MHz) with a $^{13}C$ cryoprobe (125 MHz). Spectra were assigned using a combination of $^1H$, $^{13}C$, HSQC, HMBC, COSY, and TOCSY. All chemical shifts were quoted on δ-scale in ppm, with residual solvent as internal standard. Coupling constants (J) are reported in Hertz (Hz). Infrared spectra were recorded on a Bruker Tensor 27 Fourier Transform spectrophotometer recorded in wavenumbers (cm$^{-1}$). Low-resolution mass spectra were recorded on a LCT Premier XE using electrospray ionization (ES). High-resolution mass spectra were recorded on a Bruker microTOF. Specific rotations were measured on PerkinElmer 241 polarimeter with path length of 1.0 dm and concentration (c) in g/100 mL. Thin layer chromatography (TLC) was performed on Merck EMD Kieselgel 60F$_{254}$ precoated aluminium backed plates. Reverse-phase thin layer chromatography (RF-TLC) was performed on Merck EMD Silica Gel RP-18 W F254s precoated glass backed plates. TLC and RF-TLC were visualized in combination of: 254/365 nm UV lamp; sulfuric acid (2 M in EtOH/W 1:1) [W=water]; ninhydrin (2% ninhydrin in EtOH); aqueous KMnO$_4$ (5% KMnO$_4$ in 1 M NaOH); aqueous phosphomolybdinc acid/Ce(IV) (2.5% phosphomolybdic acid hydrate, 1% cerium(IV) sulfate hydrate, and 6% H$_2$SO$_4$); or ammonium molybdate3 (5% in 2M H$_2$SO$_4$). Flash chromatography was carried out with Fluka Kiegselgel 60 220-440 mesh silica gel. All solvents (analytical or HPLC) used were purchased from Sigma Aldrich, Fisher Scientific, or Rathburn. Anhydrous solvents were purchased from Sigma Aldrich and stored over molecular sieves (<0.005% H$_2$O). Petrol refers to the fraction of petroleum ether having boiling point in the range of 40-60° C. Analytical (Synergi™ 4 μm Hydro-RP 80A 100×4.60 mm) and preparative (Synergi™ 4 μm Hydro-RP 80A 100×21.20 mm) reversed phase C18 column for HPLC were obtained from Phenomenex. Brine refers to saturated solution of NaCl.

Analytical Scale HPLC Analysis was Performed as Follows:

Analytical-scale HPLC analysis and preparative-scale HPLC purification were performed on an UltiMate 3000, and the resulting data was analysed using Chromeleon software.

Column: Phenomenex, Synergi 4u Hydro-RP 80 Å 100×4.60 mm 4 micron. Flow rate: 1 mL/min.; Solvent A: 5% ACN and 0.1% FA in H$_2$O; Solvent B: 0.1% FA in ACN; UV 260 nm. Eluent gradient (minutes/% B): 1.000/0.0; 25.000/100.0; 27.010; 100.0; 29.010/0.0; 35.010/0.0.

Preparative Scale HPLC Purification was Performed as Follows:

Column: Phenomenex, Synergi 4u Hydro-RP 80A 100×21.20 mm 4 micron. Flow rate: 12 mL/min.; Solvent A: 5% ACN and 0.1% FA in H$_2$O; Solvent B: 0.1% FA in ACN; UV 260 nm. Eluent gradient (minutes/% B): 1.000/0.0; 25.000/100.0; 27.010/100.0; 28.010/0.0; 35.010/0.0

BIOLOGICAL EXPERIMENTS

All prepared biological solutions and equipment, such as media, plastic and glassware, used in handling of the microbial cultures were autoclaved/sterilized at 121° C. for 20 minutes in LTE Scientific Ltd tabletop Touchclave® autoclave. All biological work was performed in a Bassaire laminar flow cabinet. Bacterial cultures were incubated in New Brunswick Scientific, Innova 42 Incubator Shaker Series. Centrifugation was performed in Thermo Scientific Heraeus Megafuge 40R centrifuge. Optical density was measured on BMG Labtech SPECTROstar Omega spectrophotometer or Amersham Bioscience Ultrospec 10. Water was deionized and passed through Millipore 0.22 μm filter prior to use. All human tissue culture work was carried out in a designated tissue culture room, with equipments and biosafety cabinet. Gloves and long-sleeve lab gown were worn at all times. Any bio-waste or consumable tissue culture materials were disposed in a designated auto-clave waste bin.

Mueller-Hinton (MH) broth (Oxoid) was prepared according to the manufacturer's procedure. Mueller-Hinton Agar (Oxoid) was prepared according to the manufacturer's procedure. Muller-Hinton agar plates were prepared according to CLSI standards. In this regard, Mueller-Hinton Agar (Oxoid) was prepared according to the manufacturer's procedure. 25 mL of the warm agar solution was transferred to 90 mm×16.2 mm plates via sterile pipette. The agar plate was cooled at room temperature for 15 minutes before use or storage at 4° C. up to two weeks. Stock solutions were prepared as 1.25 mg/mL or 1 mg/mL in MilliQ water or methanol, and stored at −20° C.

Bacteria used were as follows: [Test strain/(Gram+/−)/Description/Source]

*Streptomyces chartreusis*/+/NRRL3882/DSMZ

*Bacillus subtilis* EC1524/+/Tunicamycin sensitive strain/John Innes Centre

*Bacillus cereus*/+/Test strain, ATCC 11778/DSMZ

*Pseudomonas aeruginosa*/−/Standard test strain, ATCC 27853/Thermo Scientific

*Mycobacterium tuberculosis*/+/HR/NIH

Mammalian Cell Lines used were as follows:

HepG2 Human hepatocellular carcinoma cells

HEK293 Human embryonic kidney cells

Example 1: Synthesis of Lipid-Altered Tunicamycin Analogues

Lipid modified tunicamycin derivatives E1 to E7 and underlying scaffold compounds A to D were synthesized.

15
-continued
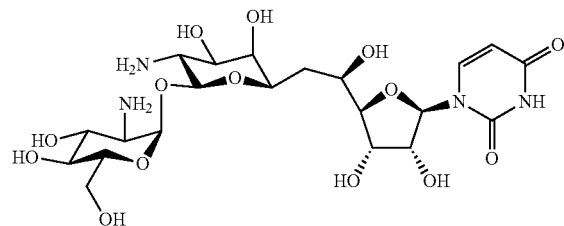
D
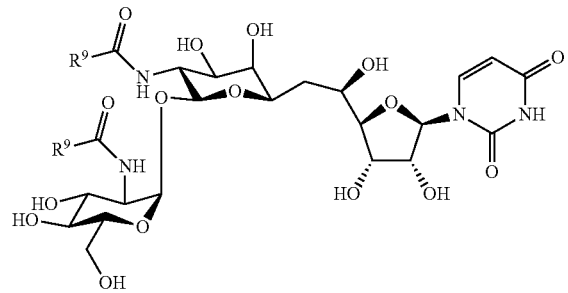
E
16
-continued
wherein
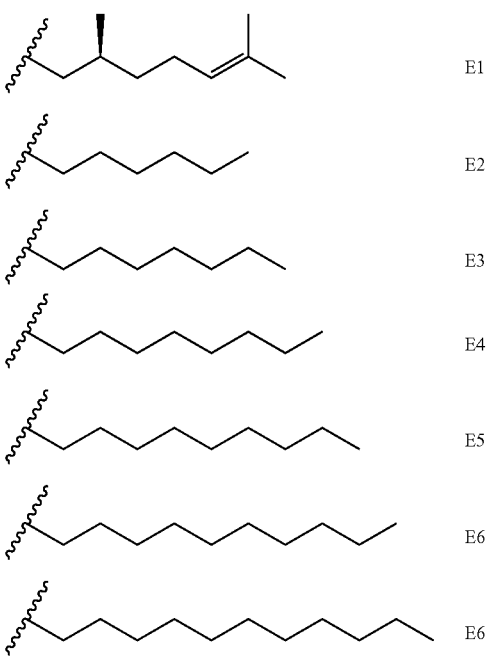
$R^9 =$
The following semi-synthetic scheme illustrates the reaction processes detailed below.
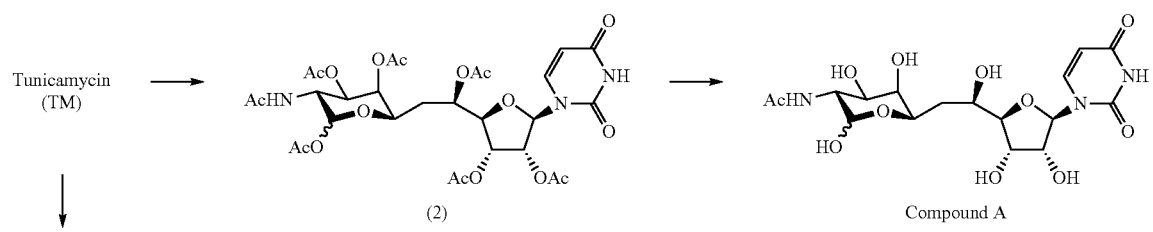
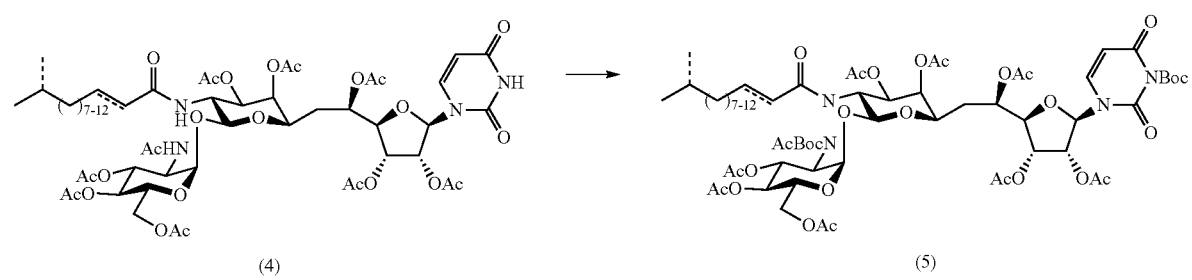

-continued

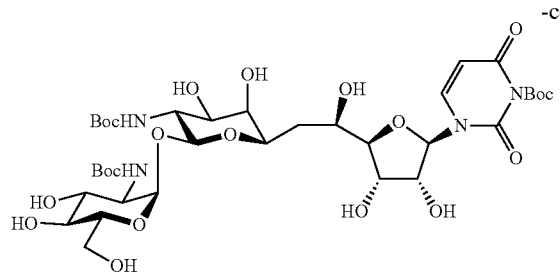

Compound B

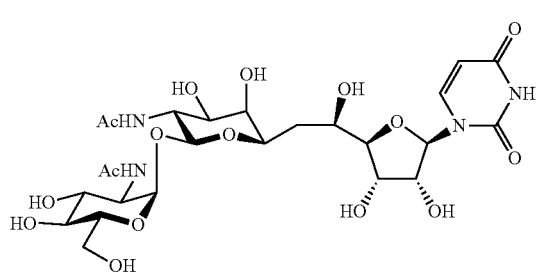

Compound C

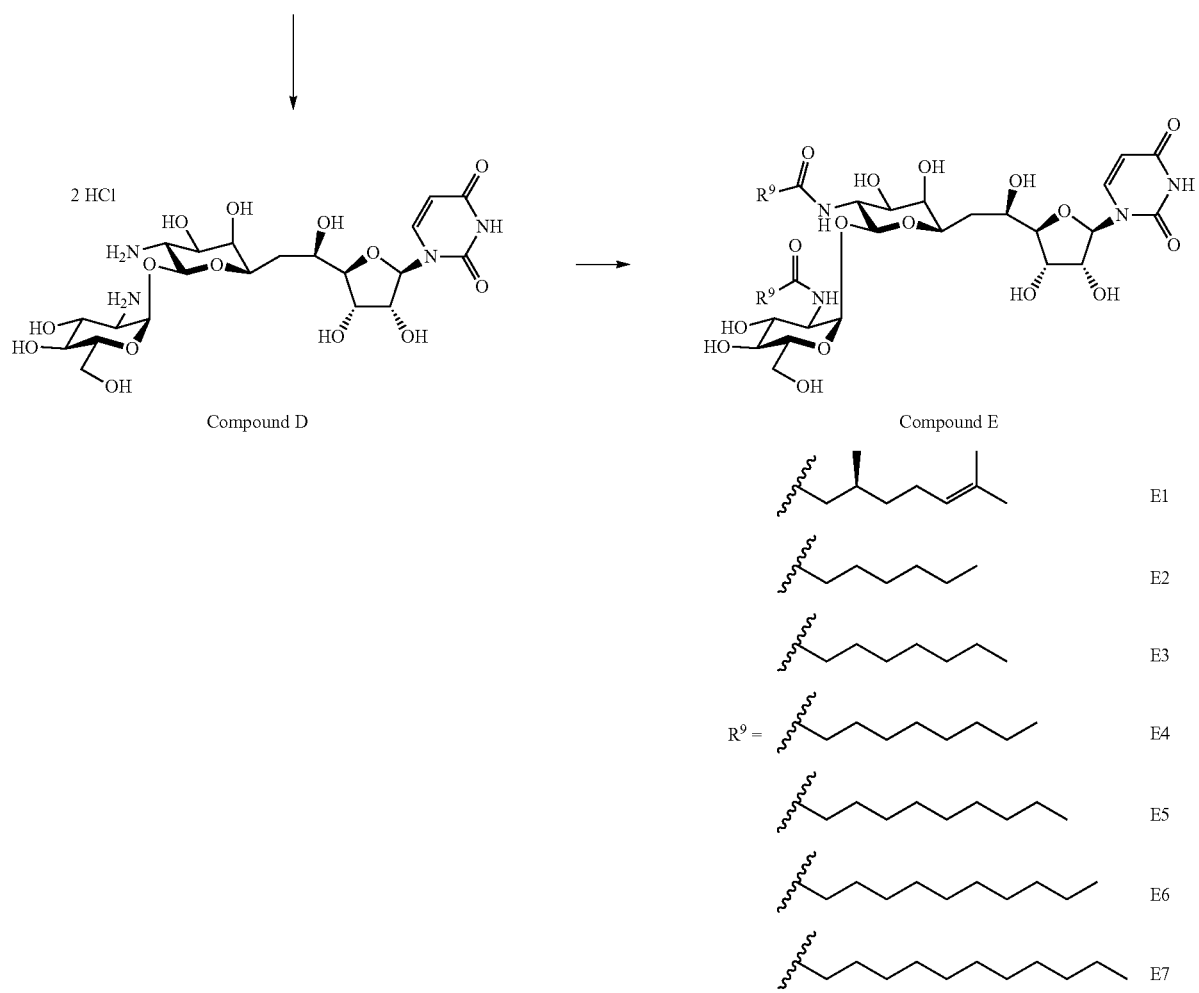

Compound D

Compound E

Tunicamycin (TM, 1)

Crude tunicamycin (TM) was isolated from *S. chartreusis* NRRL3882 fermentation culture by methanol extraction. Optimised growth and extraction processes allowed yields of 42±5 mg per litre of culture.

Figure 6:
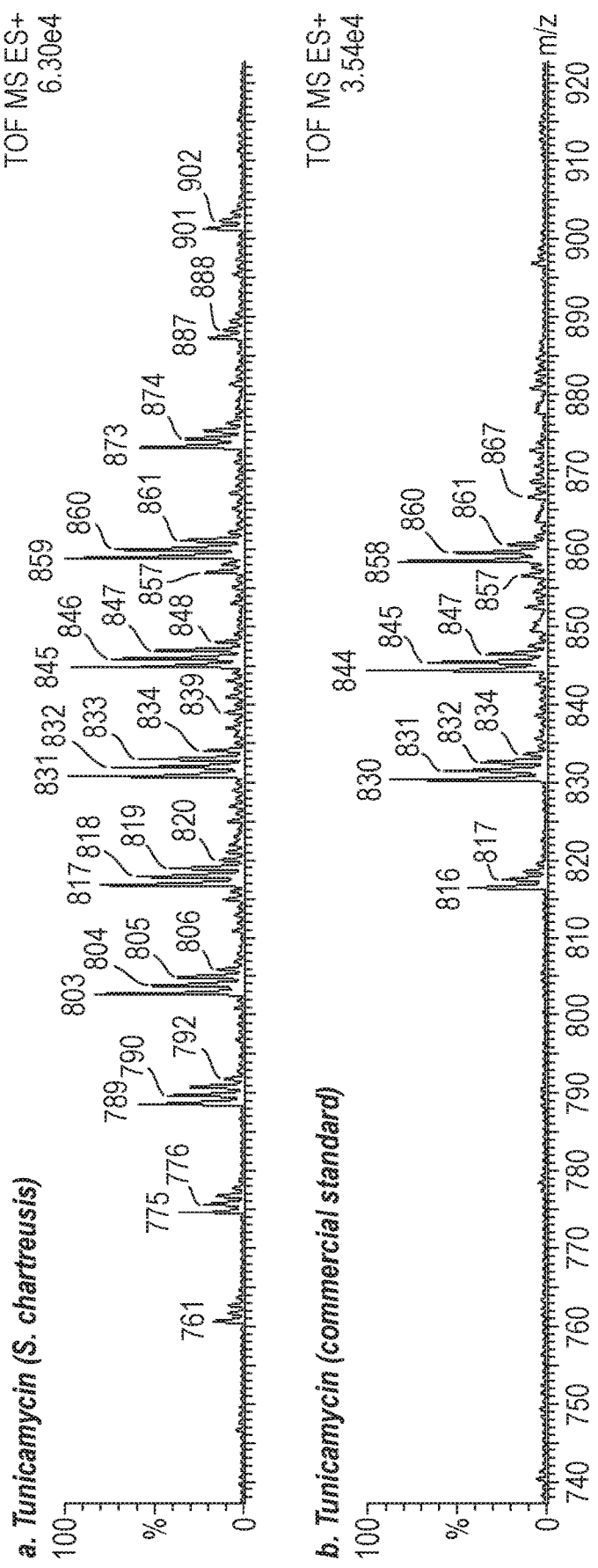
FIG. 6 shows time-of-flight mass spectra (TOF-MS) for tunicamycin obtained from two different sources.

In one example, crude tunicamycin was isolated from a *S. chartreusis* NRRL3882 fermentation culture by methanol extraction (Hamill, 1980; Takatsuki et al., 1971). *S. chartreusis* spore stock (2 µL) was added to 50 mL of TYD media in a 250 mL spring coiled flask, and incubated at 28° C. and 200 rpm in a New Brunswick Series 25 shaker. After 36 h, aliquots of this culture (12×2 mL) was added to 12×1 L of TYD media including 6 g of glucose and 0.3 g of $MgCl_2$ in unbaffled 2 L conical flasks, which were subsequently incubated at 28° C. and 200 rpm in a New Brunswick Series 25 shaker. After 7 days, cells and supernatant were separated via decantation and centrifugation at 8500 rpm (Beckman Coulter Avanti J-25). Tunicamycin was extracted from both the centrifuged cells and supernatant. Tunicamycin in the supernatant was isolated by hydrophobic interaction chromatography. Amberlite XAD-16 was first preconditioned by washing with MeOH (×3) and then distilled water (×2). This preconditioned resin (15 g/L) was then added to the resulting supernatant and stirred for 2 h. The magnetic stirrer was then turned off and the XAD-16 resin was allowed to settle to the bottom of the flask, after which the majority of the supernatant was decanted and the remaining supernatant was removed by filtration. The collected resin was washed with water (200 mL) for 15 min and filtered through filter paper, and then stirred sequentially in MeOH (600 mL, 15 min), iPrOH (600 mL, 15 min) and MeOH (600 mL, overnight). The organic fractions were combined and concentrated in vacuo. The concentrated tunicamycin solution was aliquoted into four Falcon tubes and the volume adjusted to 40 mL with 1M HCl to precipitate tunicamycin. The insoluble precipitate was collected via centrifugation, re-dissolved in MeOH and then diluted with 400 mL of acetone. The acetone solution was kept at −20° C. overnight and the precipitated crude tunicamycin collected by filtration. Tunicamycin was also extracted from the cell pellet. The pellet was stirred in 1M aq. HCl (800 mL) for 30 min, after which the cells were collected by centrifugation at 9000 rpm (Beckman Coulter Avanti J-25). This process was repeated, after which the cell pellet was stirred in MeOH (400 mL) overnight. The cells were collected by filtration, resuspended in MeOH (400 mL) and stirred for a further 4 h. The MeOH fractions were combined, concentrated in vacuo, and tunicamycin precipitated with acetone (400 mL). Crude tunicamycin: TLC: $R_f$ 0.3 in water/isopropanol/ethyl acetate (W/iPOH/EtOAc, 1:3:6); $^1$H NMR (400 MHz, CD$_3$OD) δ ppm 0.89, 0.91 (2×s, 2×3 H, —CH(CH$_3$)$_2$), 1.14-1.66 (m, n×CH$_2^{fatty\ acid}$), 1.95 (s, 3H, —CH$_3^{NHAc}$), 3.36-4.05 (m, —CH$_2^{sugar}$, CH$^{sugar}$), 4.10 (t, J=9.30 Hz, 1H, H-10'), 4.20 (t, $J_{2',1'}$=5.80 Hz, 1H, H-2'), 4.59 (d, $J_{11',10'}$=8.9 Hz, 1H, H-11'), 4.94 (d, J=3.6 Hz, 1H, H-1''), 5.77 (d, $J_{5,6}$=8.2 Hz, 1H, H-5$^{uracil}$), 5.95 (d, $J_{1',2'}$=5.5 Hz, 1H, H-1'), 5.96 (d, $J_{HC=CH\ trans}$=15.4 Hz, 1H, =CHC(O)—), 6.84 (dt, $J_{HC=CH\ trans}$=14.5 Hz, J=7.85 Hz, 1H, —CH$_2$HC=), 7.94 (d, $J_{6,5}$=8.2 Hz, 1H, H-6$^{uracil}$); LRMS m/z (ESI$^+$): [(M+Na)$^+$]=839 (18%), 853 (100%), 867 (92%), 881 (30%); (ESI$^-$): [(M+Cl)$^-$]=851 (20%), 865 (100%), 879 (94%), 893 (34%). Flanking peaks with mass±14 corresponded to 8×CH$_2$, 9×CH$_2$, 10×CH$_2$, and 11×CH$_2$. IR v: 3325, 2925, 2360, 2342, 1665, 1376, 1234, 1093, 1025; LC/MS m/z (TOF MS ES$^+$): 761, 775, 789, 803, 817, 831, 845, 859, 873, 887, 901. TOF-MS of crude tunicamycin extracted from the S. Chartruesis culture is shown in FIG. 6(a), while FIG. 6(b) shows the TOF-MS of a commercial tunicamycin standard obtained from Sigma Aldrich (Sigma Aldrich, retention time 14-19 min). Analysis of the quantity of tunicamycin obtained is shown in the Table below.

| S. chartreusis strain | Culture Vol. (L) | tunicamycin isolated$^a$ (mg) | Sample$^a$ (mg/mL) | HPLC$^b$ (mg/mL) | Purity$^c$ (%) | tunicamycin/ Liter$^d$ (mg/L) |
|---|---|---|---|---|---|---|
| NRRL3882 | 12 | 687.3 | 1.25 | 1.0296 | 82.4 | 47.2 |
| NRRL3882 | 24 | 1066.4 | 1.30 | 1.0201 | 78.5 | 34.9 |
| NRRL3882 | 12 | 1483.1 | 1.40 | 0.4718 | 33.7 | 41.7 |
| NRRL3882 | 11 | 891.1 | 1.40 | 0.7899 | 56.4 | 45.7 |

$^a$Crude sample;
$^b$Crude sample concentration injected into HPLC for analysis. tunicamycins dissolved in methanol;
$^c$Determined by HPLC, based on a standardised curve;
$^d$Purity and Culture Vol. were taken in consideration into the initial tunicamycins isolated.

The average yield of tunicamycin per litre of culture, based on the tunicamycin/Litre information above, was 42±5 mg.

Fermentation of Streptomyces chartreusis cells was also repeated on a large scale to obtain tunicamycin. When performed on a large scale, the extraction was as follows. Sterile TYD media (2 g Tryptone, 2 g yeast extract, 6 g glucose and 30 mg MgCl$_2$.6H$_2$O per litre) was added to 4×500 mL conical spring flasks. Each flask was inoculated with 50 µl of the Streptomyces chartreusis spore stock (~5×10$^7$ spores) and incubated at 28° C. with shaking on a rotary shaker (250 RPM) for 4-5 days. The flasks were then used to inoculate 90 L of TYD media in a Bioflow5000 fermenter at the University of East Anglia Fermentation Suite. Cells were fermented at 32° C. with an air flow rate of 0.25 L/L/min for 5-7 days before being harvested. Tunicamycin was extracted from resulting mycelial cake as described above.

Heptaacetyl-tunicamyl-uracil, (2)

Crude TM (103 mg, 0.123 mmol) was suspended in 3 M aq. HCl (2 mL) and stirred under reflux at 105° C. for 3 hr. After 3 hr. the solvent was co-evaporated with toluene in vacuo. The residue was re-dissolved in dry pyridine (3 mL) and Ac$_2$O (2 mL). After 18 hr. of stirring at RT, TLC showed a product spot with $R_f$ 0.3. After solvent was evaporated in vacuo, flash chromatography (MeOH/EtOAc, 1:19) afforded 2 (21 mg, 0.030 mmol, 25%).

N-acetyl-tunicamyl-uracil Compound A

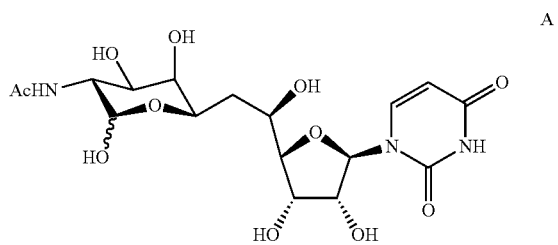

Heptaacetyl-tunicamyl-uracil (2) (41.4 mg, 0.059 mmol) was dissolved in dry MeOH (5 mL), stirred and cooled to 0° C. NaOMe was added to make a final concentration of 0.01 M. Reaction was monitored by TLC (1:2:2, W/iPOH/EtOAc). Reaction was neutralized after 3 hr. with Dowex 50 W×8 H$^+$ resin. Reaction solution filtered and concentrated in vacuo. Flash chromatography (W/iPOH/EtOAc, 1:2:2) afforded the product A (25.9 mg, 0.058 mmol, 98%).

Octa-O-acetyl-tunicamycin (4)

Crude TM (682 mg, 0.814 mmol) was dissolved in dry pyridine (5 mL) with an addition of Ac$_2$O (3 mL). After stirring at RT for 18 hours TLC (EtOAc) showed a major product at $R_f$ 0.4 (4). The solvent was evaporated in vacuo and purified via flash chromatography (MeOH/DCM, 3:97) to afford the product 4 (782 mg, 0.667 mmol, 82%) as clear glass.

TLC: $R_f$ 0.4 in methanol/dichloromethane (MeOH/DCM, 3:97); $^1$H NMR (500 MHz, CD$_3$OD) δ ppm 7.48 (d, $J_{6,5}$=8.0 Hz, 1H, H-6$^{uracil}$), 6.83 (dt, $J_{HC=CH\ trans}$=14.2 Hz, J=7.3 Hz, 1H, C=CH—CH$_2$), 5.87 (d, $J_{HC=CH\ trans}$=15.5 Hz, 1H, C=CH—CO), 5.81 (d, $J_{1',2'}$=5.1 Hz, 1H, H-1'), 5.75 (d, $J_{5,6}$=8.0 Hz, 1H, H-5$^{uracil}$), 5.56 (dd, $J_{3',2'}$=6.1 Hz, $J_{3',4'}$=5.5 Hz, 1H, H-3'), 5.51 (dd, $J_{2',1'}$=$J_{2',3}$=5.3 Hz, 1H, H-2'), 5.26 (dd, $J_{3'',2''}$=10.6 Hz, $J_{3'',4''}$=9.9 Hz, 1H, H-3''), 5.27 (ddd, $J_{5',6'}$=9.7 Hz, $J_{5',4'}$=6.8 Hz, J=3.6 Hz, 1H, H-5'), 5.11 (dd, $J_{8',9'}$=9.7 Hz, $J_{8',7'}$=7.3 Hz, 1H, H-8'), 5.07 (app t, $J_{4'',5''}$=11.3 Hz, $J_{4'',3''}$=3.2 Hz, 1H, H-4''), 5.03 (dd, $J_{9',10'}$=3.6 Hz, $J_{9',8'}$=3.2 Hz, 1H, H-9'), 4.98 (d, $J_{1'',2''}$=4.9 Hz, 1H, H-1''), 4.75 (d, $J_{11',10'}$=8.4 Hz, 1H, H-11'), 4.33 (dd, $J_{6a'',6}$b''=11.1

Hz, $J_{6'',5''}$=3.9 Hz, 1H, H-6''), 4.34 (dd, $J_{10',9'}$=4.6 Hz, $J_{10',11'}$=3.6 Hz, 1H, H-10'), 4.32 (ddd, $J_{5'',4''}$=10.4, $J_{5'',6''}$=2.9 Hz, $J_{5'',6''}$=2.2 Hz, 1H, H-5''), 4.20 (dd, $J_{4',3'}$=7.7 Hz, $J_{4',5'}$=3.6 Hz, 1H, H-4'), 4.19 (dd, $J_{2'',3''}$=7.2 Hz, $J_{2'',1''}$=3.1 Hz, 1H, H-2''), 4.19 (dd, $J_{6a'',6b''}$=14.2 Hz, $J_{6'',5''}$=2.6 Hz, 1H, H-6''), 3.92 (ddd, J=9.4 Hz, $J_{7',6'}$=3.8 Hz, $J_{7',8'}$=3.1 Hz, 1H, H-7'), 2.22 (s, 3H, $CH_3^{Ac}$), 2.17 (m, 2H, —$CH_2CH$=C), 2.14 (s, 6H, 2×$CH_3^{Ac}$), 2.10 (s, 3H, $CH_3^{Ac}$), 2.06 (m, 2H, H-6'), 2.04, 2.03, 1.98, 1.95, 1.89 (5×s, 5×3 H, 5×$CH_3^{Ac}$), 1.78 (ddd, $J_{6b',a}$=14.8 Hz, $J_{6',5'}$=8 Hz, $J_{6',7'}$=3.3 Hz, 1H), 1.55 (spt, J=6.7 Hz, 1H, —$CH(CH_3)_2$), 1.46 (quin, J=6.8 Hz, 2H, —$CH_2CH_2CH$=C), 1.23-1.37 (m, 14H, —$CH_2^{acyl}$), 1.18 (dt, J=13.1, 7.0 Hz, 2H, $CH_2CH(CH_3)_2$), 0.91, 0.89 (2×s, 2×3 H, —$CH(CH_3)_2$); $^{13}$C NMR (126 MHz, $CD_3OD$) δ ppm 173.2, 172.4, 172.3, 172.3, 172.0, 171.7, 171.5, 171.3, 171.2 ($C=O^{Ac}$, $C=O^{NHAc}$), 169.5 ($C=O^{acyl}$), 165.9 (C-4 C=O), 151.8 (C-2 C=O), 147.7 (C=CH—$CH_2$), 143.4 (C-$6^{uracil}$), 124.2 (C=CH—CO), 103.5 (C-$5^{uracil}$), 101.6 (C-11'), 100.0 (C-1''), 91.1 (C-1'), 84.1 (C-4'), 73.5 (C-2'), 72.2 (C-3''), 72.2 (C-9'), 71.7 (C-7'), 70.9 (C-3'), 70.8, 70.3 (C-5', C-8'), 69.8 (C-5''), 69.7 (C-4''), 63.0 (C-6''), 52.6 (C-2''), 51.8 (C-10'), 40.3 (—$CH_2CH(CH_3)_2$), 33.2 (—$CH_2CH$=C), 33.1 (C-6'), 30.3-31.1 (5×-$CH_2^{acyl}$), 29.4 (—$CH_2CH_2CH$=C), 29.2 (—$CH(CH_3)_2$), 28.6 (—$CH_2^{acyl}$), 23.0, 23.1 (—$CH(CH_3)_2$), 22.9 (—$CH_3^{NHAc}$), 21.1 (—$CH_3^{Ac}$), 20.7 (2×-$CH_3^{Ac}$), 20.6, 20.6, 20.6, 20.6, 20.3 (5×-$CH_3^{Ac}$); IR v: 2927, 2361, 2341, 1745, 1696, 1540, 1369, 1219, 1031; MS m/z (ESI$^+$): 1203 [(M+Na)$^+$, 100%]; (ESI$^-$): 1179 [(M+Cl)$^-$, 100%]. Flanking peaks with mass±14 corresponded to 8×$CH_2$, 9×$CH_2$, 10×$CH_2$, and 11×$CH_2$. Full assignment was not possible due to the presence homologues with mass±14.

Tri-N-(tert-butoxylcarbonyl)-octa-O-acetyl-tunicamycin (5)

In order to cleave the lipid chain, the tert-butoxylcarbonyl (Boc) protecting group was added to the secondary amides at positions 3, 10', and 2'' to afford the tri-N-Boc-octa-O-acetylated tunicamycins. Amide cleavage usually involves the use of a strong acid or base and high temperatures, but these harsh conditions would be unsuitable to use in the presence of the uridine moiety as they would degrade the tunicamycins. Several methodologies have been published on how to remove the highly stable and unreactive acetyl group. One of them is Kunieda's mild N-bocylation methodology. Attachment of Boc group to the secondary amide increases the electrophillicity of carbonyl, allowing the acetyl group to be readily cleaved in the presence of a base.

In one instance of the formation of (5), octa-O-acetyl-tunicamycin 4 (101 mg, 0.086 mmol) was dissolved in dry THF (1.5 mL) with the addition 4-(dimethylamino)pyridine (2.10 mg, 0.017 mmol) and di-tert-butyl dicarbonate (750 mg, 3.44 mmol) with 10 eq. added over time. The reaction flask was fitted over an oven dried condenser and heated to 60° C. with stirring. After 36 hr. TLC (EtOAc/Petrol, 6:4) showed $R_f$ 0.3 and 0.1. The reaction was cooled and the solvent was evaporated in vacuo. Flash chromatography (EtOAc/Petrol, 6:4) afforded the product 5 (67.1 mg, 0.045 mmol, 53%) as yellow glass.

In another instance, octa-O-acetyl-tunicamycin 4 (101 mg, 0.086 mmol) was dissolved in dry THF (1.5 mL) with the addition of 4-(dimethylamino)pyridine (10.5 mg, 0.086 mmol) and di-tert-butyl dicarbonate (187.7 mg, 0.86 mmol). The reaction mixture was heated to 60° C. with stirring for 4 h, and subsequently another portion of di-tert-butyl dicarbonate (187.7 mg, 0.86 mmol) was added to the reaction mixture, with stirring continued for an additional 2 h. After a total of 6 h, the reaction mixture was checked by TLC (EtOAc/Petrol, 6:4). This which showed the formation of two products:

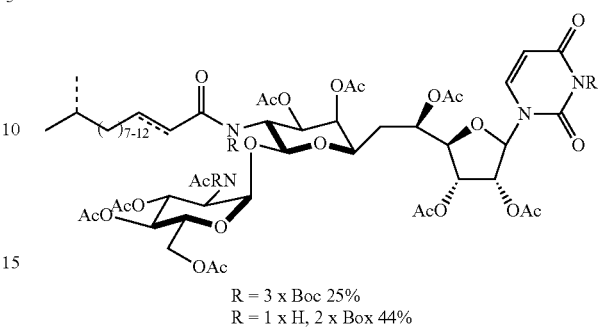

R = 3 x Boc 25%
R = 1 x H, 2 x Box 44%

Compound 5 ($R_f$ 0.3) and tunicamycin-8OAc-2Boc ($R_f$ 0.1). The reaction mixture was concentrated in vacuo and purified by flash column chromatography (EtOAc/Petrol, 6:4). Compound 5 (31.1 mg, 0.021 mmol, 25%) was obtained as a yellow glass and tunicamycin-8OAc-2Boc (52.4 mg, 0.038 mmol, 44%) as a yellow oil; compound 5: TLC: $R_f$ 0.5 in ethyl acetate/petrol (EtOAc/Petrol, 6:4); $^1$H NMR (500 MHz, CDCl$_3$) δ ppm 7.48 (d, $J_{6,5}$=8.0 Hz, 1H, H-$6^{uracil}$), 6.89 (dt, $J_{HC=CH\ trans}$=15.1 Hz, J=6.9 Hz, 1H, C=CH—$CH_2$), 6.82 (dt, $J_{HC=CH\ trans}$=14.5 Hz, J=7.6 Hz, 1H, C=CH—$CH_2$), 6.39 (d, $J_{HC=CH\ trans}$=15.1 Hz, 1H, C=CHCO), 6.27 (d, $J_{HC=CH\ trans}$=15.4 Hz, 1H, C=CH—CO), 6.11 (m, 1H, C—$H^{anomeric}$), 5.85 (m, 1H, $CH^{anomeric}$, H-$5^{uracil}$), 5.83 (d, J=8.2 Hz, 1H, H-$5^{uracil}$), 5.61 (dd, J=11.5 Hz, J=3.3 Hz, 1H), 5.53 (dd, J=11.3 Hz, J=3.5 Hz, 1H), 5.49 (d, J=8.2 Hz, 1H), 5.43 (m, 1H), 5.29-5.35 (m, 1H), 5.09-5.25 (m, 4H), 5.01-4.10 (m, 1H), 4.99 (d, J=9.1 Hz), 4.94 (dd, J=11.5 Hz, J=3.3 Hz, 1H), 4.91 (s, 1H), 4.52-4.60 (m, 1H), 4.30-4.39 (m, 1H), 4.17 (d, J=10.4 Hz, J=2.2 Hz, 1H), 4.05-4.10 (m, 1H), 3.76 (dd, J=8.8 Hz, J=3.5 Hz, 1H), 3.68 (dd, J=9.9 Hz, J=2.0 Hz, 1H), 2.34 (s, 1H), 2.29 (s, 2H, $CH_3^{NHAc}$), 2.27 (s, 1H, $CH_3^{NHAc}$), 1.87-2.22 (m, 24H, 8×$CH_3^{Ac}$), 1.59, 1.56, 1.55, 1.53, 1.52 (5×s, 27H, 9×$CH_3^{Boc}$), 1.40 (m, 13H), 1.08-1.18 (m, 2H, $CH_2^{acyl}$), 0.86, 0.85 (2×s, 2×3 H, $CH_3^{acyl}$); $^{13}$C NMR (126 MHz, $CD_3OD$) δ ppm 177.4, 177.5, 170.8, 170.7, 170.1, 169.9, 169.7, 169.6, 169.5, 169.4, 169.1 (C=O), 168.2 (C-4 C=O), 159.8 (C-2 C=O), 153.0, 152.9, 157.7, 152.7, 152.1, 148.3, 148.1, 147.3, 139.1, 139.0, 138.9 (C=CH—$CH_2$, C-$6^{uracil}$), 124.4, 123.9 (C=CH—CO), 103.5, 103.2 (C-1''), 97.8, 87.7, 86.9, 87.0, 86.9, 86.3, 82.4, 82.3, 72.1, 70.4, 70.2, 70.1, 69.6, 69.5, 69.4, 69.2, 69.1, 68.8, 68.0, 67.9, 61.5, 61.4, 57.657.0, 54.8, 39.0, 38.5, 36.6, 34.3, 32.7, 32.5, 32.4, 31.9, 29.9, 29.6, 29.5, 29.4, 29.3, 29.2, 28.2, 28.0, 27.9, 27.8, 27.6, 27.4, 22.6, 20.9, 20.9, 20.7, 20.6, 20.5, 20.4 (C-1'), 84.1 (C-4'), 73.5 (C-2'), 72.2 (C-3''), 72.2 (C-9'), 71.7 (C-7'), 70.9 (C-3'), 70.8, 70.3 (C-5', C-8'), 69.8 (C-5''), 69.7 (C-4''), 63.0 (C-6''), 52.6 (C-2''), 51.8 (C-10'), 40.3 (—$CH_2CH(CH_3)_2$), 33.2 (—$CH_2CH$=C), 33.1 (C-6'), 30.3-31.1 (5×C, 5×-$CH_2^{acyl}$), 29.4 (—$CH_2CH_2CH$=C), 29.2 (—$CH(CH_3)_2$), 28.6 (—$CH_2^{acyl}$), 23.0, 23.1 (2×C, —$CH(CH_3)_2$), 22.9 (—$CH_3^{NHAc}$), 21.1 (—$CH_3^{Ac}$), 20.7 (2×C, 2×-$CH_3^{Ac}$), 20.6, 20.6, 20.6, 20.6, 20.3 (5×C, 5×-$CH_3^{Ac}$) IR v: 2928, 2361, 2341, 1743, 1686, 1369, 1218, 1143, 1029; LRMS m/z (ESI$^+$): 1503 [(M+Na)$^+$, 100%]; (ESI$^-$): 1515 [(M+Cl)$^-$, 100%]. Flanking peaks with mass±14 corresponded to 8×$CH_2$, 9×$CH_2$, 10×$CH_2$, and 11×$CH_2$.

10',2"-Di-N-Boc-α-D-glucosamine-(1"-11')-tunicamyl Uracil Compound B

α-D-N-acetylglucosamine-(1"-11')-N-acetyl Tunicamyl Uracil Compound C

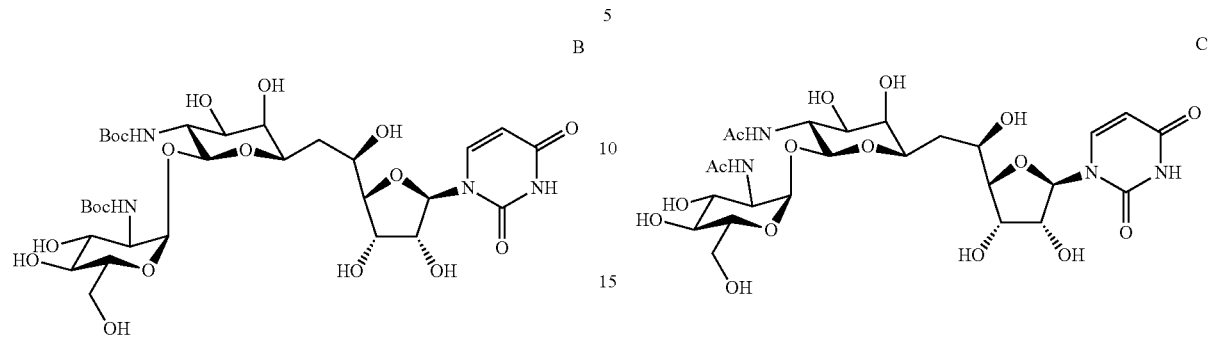

In one instance, tri-N-(tert-butoxylcarbonyl)-octa-O-acetyl-tunicamycin 5 (134 mg, 0.091 mmol) was dissolved in MeOH:$H_2O$ (v/v, 1:1) with the addition of TEA (25 equiv. 2.27 mmol, 317 The reaction was heated to 71° C. The reaction progress was monitored by TLC (1:2:6, W/iPOH/EtOAc). Reaction was complete after 43 hours. The crude product was purified by preparative scale HPLC and afforded the product B (36.4 mg, 0.047 mmol, 52%) as white amorphous powder.

In another instance, tri-N-(tert-butoxylcarbonyl)-octa-O-acetyl-tunicamycin 5 (134 mg, 0.091 mmol) was dissolved in MeOH:$H_2O$ (v/v, 3:1) with the addition of TEA (25 equiv. 2.27 mmol, 317 μl). The reaction mixture was heated to 71° C. and reaction progress monitored by TLC (1:2:6, W/iPrOH/EtOAc). After 43 h the mixture was directly purified by preparative scale HPLC (retention time 9.5 min). Product containing fractions were pooled and lyophilized to afford Compound B (36.4 mg, 0.047 mmol, 52%) as white amorphous powder; TLC: $R_f$ 0.3 in water/isopropanol/ethyl acetate (W/iPOH/EtOAc, 1:2:6); $R_f$=0.3 ($H_2$O/iPrOH/EtOAc, 1/2/7); $[α]_D^{20}$=+54.9±0.3 (c 1, MeOH); Mp (amorphous) 177.4-181.2° C.; $^1$H NMR (500 MHz, $CD_3OD$) δ ppm 7.91 (d, J=8.1 Hz, 1H, H-6), 5.93 (d, J=5.9 Hz, 1H, H-1'), 5.75 (d, J=8.1 Hz, 1H, H-5), 4.99 (s, 1H, H-1"), 4.70 (d, J=7.9 Hz, 1H, H-11'), 4.24-4.16 (m, 2H, H-2', H-3'), 4.05-3.97 (m, 2H, H-5', H-5"), 3.86 (t, J=3.3 Hz, 1H, H-4'), 3.81 (dd, J=11.7, 1.8 Hz, 1H, H-6"), 3.77-3.65 (m, 3H, H-7', H-9', H-6"), 3.64 (d, J=3.1 Hz, 1H, H-8'), 3.62 (d, J=4.9 Hz, 2H, H-2", H-3"), 3.49 (t, J=9.6 Hz, 1H, H-10'), 3.37-3.33 (m, 1H, H-4"), 2.12-2.05 (m, 1H, H-6'), 1.57-1.49 (m, 1H, H-6'), 1.47 (s, 9H, $CH_3$), 1.45 (s, 9H, $CH_3$); $^{13}$C NMR (126 MHz, $CD_3OD$) δ ppm 166.2 (C-4), 158.7 (C=$O^{Boc}$), 158.5 (C=$O^{Boc}$), 152.6 (C-2), 142.8 (C-6), 103.1 (C-5), 101.4 (C-11'), 100.6 (C-1"), 89.7 (C-1'), 89.5 (C-4'), 80.7 (C—($CH_3$)$_3$), 80.3 (C—($CH_3$)$_3$), 75.5 (C-2'), 74.5 (C-5"), 73.6 (C-3"), 72.7, 72.6, 72.4 (C-7', C-9', C-4"), 72.3 (C-8'), 70.9 (C-3'), 68.4 (C-5'), 63.2 (C-6"), 56.6 (C-4"), 55.8 (C-10'), 35.9 (C-6'), 29.1 (($CH_3$)$_3$), 28.8 (($CH_3$)$_3$); IR (neat) v: 3367 (N—H, O—H), 2979 (=C—H), 2930 (—C—H), 1684 (C=O); LRMS m/z (ESI$^+$): 789 [(M+Na)$^+$, 100%]; FIRMS m/z (ESI$^+$): calc. $C_{31}H_{50}N_4O_{18}Na$ (M+Na)$^+$=789.3012, found 789.3017.

In one instance, compound 5 (127 mg, 0.086 mmol) was dissolved in dry MeOH (5 mL), stirred and cooled to 0° C. NaOMe was added to make final concentration of 0.01 M, and monitored by TLC (1:3:6, W/iPOH/EtOAc). The reaction was neutralized after 4 hr. with Dowex 50 W×8 H$^+$ resin. Then filtered and concentrated in vacuo, and redissolved in TFA (1 mL) and stirred at RT for 1 hr. TFA was coevaporated with toluene and then redissolved in MeOH (5 mL) with the addition of $Ac_2O$ (1 mL). Reaction was stirred at RT for 12 hr. and neutralized to pH 6-7 with Dowex Marathon A $^-$OH resin, and stirred for additional 1 hr. Reaction solution was filtered and purified via flash chromatography (W/iPOH/EtOAc, 1:2:2) to afford N$^{11'}$-acetyl-N$^{11'}$-deacyl-tunicamcyin C (13.1 mg, 0.020 mmol, 23%) as yellow glass.

In another instance, compound 5 (127 mg, 0.086 mmol) was dissolved in dry MeOH (5 mL) and cooled to 0° C. NaOMe was added to a final concentration of 0.01 M and reaction progress monitored by TLC (1:3:6, W/iPOH/EtOAc). The reaction was neutralized after 4 h by addition of Dowex 50 W×8 H$^+$ resin in parts until pH 7. The mixture was then filtered, the resin washed with methanol and the combined organics and concentrated in vacuo. The resulting solid was dissolved in TFA (1 mL) and stirred at RT for 1 h. The TFA was coevaporated with toluene and the crude material then redissolved in MeOH (5 mL) and $Ac_2O$ (1 mL). The reaction mixture was stirred at RT for 12 h, neutralized to pH 6-7 with Dowex Marathon A—OH resin and stirred for an additional 1 h. The reaction mixture was filtered, concentrated in vacuo and purified by flash column chromatography (W/iPOH/EtOAc, 1:2:2) to afford compound C (13.1 mg, 0.020 mmol, 23%) as yellow glass; TLC: $R_f$ 0.3 (W/iPOH/EtOAc, 1:2:2); $[α]_D^{23}$=+50.7 (c=0.7, $H_2O$); $^1$H NMR (500 MHz, $CD_3OD$) δ ppm 7.76 (d, $J_{6,5}$=7.9 Hz, 1H, H-6$^{uracil}$), 5.84 (d, $J_{1',2'}$=7.9 Hz, 1H, H-1'), 5.83 (d, $J_{5,6}$=5.4 Hz, 1H, H5$^{uracil}$), 4.98 (d, $J_{1'',2''}$=3.5 Hz, 1H, H-1"), 4.58 (d, $J_{11',10'}$=8.5 Hz, 1H, H-6$^{uracil}$), 4.25 (dd, $J_{2',1'}$=5.4 Hz, $J_{2',3'}$=9.1 Hz, 1H, H-2'), 4.22 (dd, $J_{3',4'}$=3.5 Hz, $J_{3',2'}$=5.7 Hz, 1H, H-3'), 4.08-4.03 (m, 2H, H-4', H-5'), 3.87 (dd, $J_{10',9'}$=10.7 Hz, $J_{10',11'}$=8.5 Hz, 1H, H-10'), 3.82-3.82 (m, 1H, H-4"), 3.80 (dd, =3.8 Hz, $J_{2'',3''}$=10.7, 1 H, H-2"), 3.77 (d, J=10.1 Hz, 1H, H-7'), 3.73-3.67 (m, 2×1 H, H-8', H-6"), 3.70 (dd, $J_{3'',2''}$=10.7 Hz, $J_{3'',4''}$=3.2 Hz, 1H, H-3"), 3.68-3.41 (m, 2H, H-6", H-9'), 3.44 (app t, $J_{5'',6a''}$=9.8 Hz, 1H, H-5"), 1.98, 1.94 (2×s, 2×3H, 2×-$CH_3^{NHAc}$), 1.94 (dd, $J_{6b',6a'}$=6.6 Hz, $J_{6b',5'}$=3.2 Hz, 1H, H-6'), 1.57 (app t, $J_{6a',6b'}$=$J_{6a',5'}$=13.2 Hz, 1H, H-6a'); $^{13}$C NMR (126 MHz, $CD_3OD$) δ ppm 174.5, 174.1 (C=$O^{NHAc}$), 166.2 (C-4, C=O), 151.8 (C-2, C=O), 141.9 (C-6$^{uracil}$), 102.5 (C-5$^{uracil}$), 99.8 (C-11'), 98.3 (C-1"), 88.5 (C-1'), 87.2 (C-4'), 73.4 (C-2'), 72.6 (C-4"), 71.3 (C-7'), 71.1, 70.4, 69.8 (C-3", C-8', C-9'), 69.6 (C-5"), 68.9 (C-3'), 67.0 (C-5'), 60.4 (C-6"), 53.4 (C-2"), 52.8 (C-10'), 33.5 (C-6'), 22.2, 22.1 (2×-CH$_3^{NHAc}$); IR (neat) v: 3344, 2362, 2341, 2110, 1636, 1371, 1216; LRMS m/z (ESI$^+$): 673.26 [(M+Na)$^+$, 23%]; (ESI$^-$): 649.23 [(M−H)$^-$, 100%]; HRMS m/z (ESI+): calc. for C$_{25}$H$_{38}$N$_4$NaO$_{16}$ (M+Na)$^+$=673.2175, found 673.2195.

α-D-glucosamine-(1"-11')-tunicamyl Uracil Dihydrochloride Compound D

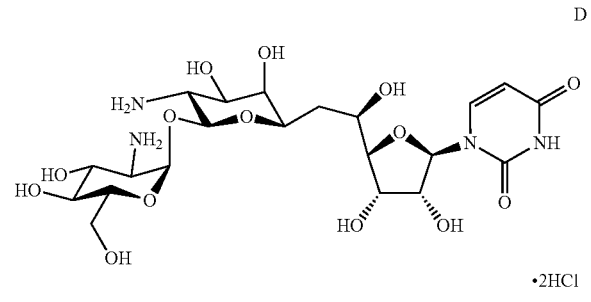

D

•2HCl

In one instance, 10',2"-Di-N-Boc-α-D-glucosamine-(1"-11')-tunicamyl uracil Compound B (64.6 mg, 0.085 mmol) was dissolved in DCM (1 mL) and TFA (50 equiv. 323 µL). The reaction was stirred at room temperature for 1 hr. The reaction progress was monitored by TLC (1:2:2, W/iPOH/EtOAc). When the reaction was complete, the reaction mixture was concentrated in vacuo and dried. The dried crude product was washed twice with H$_2$O and DCM. Aqueous fraction was collected, concentrated in vacuo and dried. The dried crude product was redissolved in 1 M HCl (1 mL) and stirred for 1 hr. at room temperature. The product D was obtained after lyophilisation, resulted in 93% yield (50 mg, 0.078 mmol).

In another instance, to a solution of Compound B (1.50 mg, 0.002 mmol) in DCM (120 µL) was added TFA (0.393 mmol 30 µL). The reaction mixture was stirred at room temperature for 1 h, with reaction progress monitored by TLC (1:2:2, W/iPOH/EtOAc). When the reaction was complete, the reaction mixture was concentrated in vacuo. The crude product was washed twice with H$_2$O and DCM, the aqueous fraction collected and concentrated in vacuo. The dried crude product was then redissoved in 1 M HCl (1 mL), stirred for 1 h at room temperature and lyophilized to yield the product D (1.20 mg, 99%). [α]$_D$20=+60.1±0.2 (c 1, H$_2$O); $^1$H NMR (700 MHz, D$_2$O) δ ppm 7.82 (d, J=8.2 Hz, 1H, H-6), 5.87 (d, J=8.2 Hz, 1H, H-5) 5.86 (d, J=5.3 Hz, 1H, H-1'), 5.53 (d, J=3.4 Hz, 1H, H-1"), 5.00 (d, J=8.3 Hz, 1H, H-11'), 4.31-4.26 (m, 2H, H-2', H-3'), 4.06 (td, J=2.6, 11.1 Hz, 1H, H-5'), 3.94 (dd, J=3.3, 11.0 Hz, 1H, H-9'), 3.92-3.87 (m, 3H, H-7', H-3", H-5"), 3.84 (d, J=3.2 Hz, 1H, H-8'), 3.79 (dd, J=3.8, 12.5 Hz, 1H, H-6"), 3.70 (dd, J=2.2, 12.4 Hz, 1H, H6"), 3.57 (t, J=9.6 Hz, 1H, H-4"), 3.39 (dd, J=3.5, 10.8 Hz, 1H, H-2"), 3.31 (dd, J=8.4, 11.0 Hz, 1H, H-10'), 1.97 (ddd, J=2.0, 10.4, 14.6 Hz, 1H, H-6'), 1.70-1.64 (dtd, J=2.8, 11.2 Hz, 1H, H-6'); $^{13}$C NMR (176 MHz, CD$_3$OD) δ ppm 166.17 (C-4), 151.8 (C-2), 142.0 (C-6), 102.4 (C-5), 99.4 (C-11'), 97.0 (C-1'), 88.7 (C-1"), 86.9 (C-4'), 73.4 (C-2'), 73.2 (C-5"), 71.8 (C-7'), 69.5 (C-8'), 69.3 (C-3"), 69.2 (C-9'), 68.9 (C-4'), 68.7 (C-3'), 66.9 (C-5'), 59.8 (C-6'), 53.8 (C-2"), 53.0 (C-10'), 33.3 (C-6'); IR (neat) v: 3295 (N—H, O—H), 3057 (=C—H), 2922 (—C—H), 1673 (C=O), 1263 (C—N), 1109 (C—O), 1064 (C—O); LRMS m/z (ESI$^+$): 567 [(M+H)$^+$, 100%]; HRMS m/z (ESI$^+$): calc. C$_{21}$H$_{35}$N$_4$O$_{14}$ (M+H)$^+$=567.2144, found 567.2136.

General Protocol for Preparing Tunicamycin Analogues

Methods for preparing the tunicamycin analogues E1, E2, E3, E4, E5, E6 and E7 are described hereafter. An exemplary general protocol for preparation of these and any other tunicamycin analogues was as follows. HATU (2.5 equiv) was added to a solution of the appropriate carboxylic acid (2.5 equiv), EDC (2.5 equiv) and DIPEA (2.5 equiv) in dry DMF. The reaction mixture was stirred at RT for 10 min, followed by the addition of Compound D (1 equiv) and DIPEA (2.5 equiv). The reaction mixture was stirred at RT for 2~4 h, diluted with a mixture of ACN/iPOH/Water (1:1:1) and purified by preparative HPLC.

Di-N-citronoyl-tunicamycin (E1)

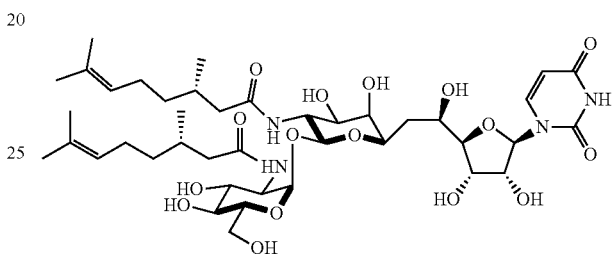

(S)-(−)-citronellic acid (5.0 µL, 0.027 mmol, 2.5 equiv) and DIC (4.2 µL, 0.027 mmol, 2.5 equiv) were added to DMF (0.25 mL) with the addition of TEA (2 µL) and DMAP (2.7 mg, 0.022 mmol, 2 equiv.) and stirred at room temperature for one hour. Then, α-D-glucosamine (1"-11')-tunicamyl uracil dihydrochloride Compound D (7 mg, 0.11 mmol) was dissolved in DMF (0.25 mL) with the addition of TEA (4.1 µL), and added to the citronellic acid reaction mixture. TEA was added to final of 4 equivalents. The reaction mixture was stirred at room temperature. The reaction progress was checked by TLC (1/3/6, H$_2$O/iPrOH/EtOAc) and HPLC. The reaction was stopped after 68 hours. The product was purified by HPLC, eluted at 14 min. The lyophilised product was washed with DCM and MilliQ water and resulted in 5.1 mg of the final product, 54% yield. R$_f$=0.4 (1/3/6, H$_2$O/iPrOH/EtOAc); [α]$_D^{20}$=+45.2±0.2 (c 0.4, MeOH); $^1$H NMR (500 MHz, MeOD) δ ppm 7.91 (d, J=8.1 Hz, 1H, H-6), 5.92 (d, J=5.9 Hz, 1H), H-1'), 5.75 (d, J=8.1 Hz, 1H, H-5), 5.11 (td, J=7.0, 1.0 Hz, 2H, H-5'"), 4.96 (d, J=3.4 Hz, 1H, H-1"), 4.58 (d, J=8.5 Hz, 1H, H-11'), 4.24-4.15 (m, 2H, H-2', H-3'), 4.06-3.95 (m, 3H, H-5', H-10', H-5"), 3.91 (dd, J=10.6, 3.5 Hz, 1H, H-2"), 3.87-3.80 (m, 2H, H-4', H-6"), 3.76 (appt dd, J=9.5, 1.9 Hz, 1H, H-7'), 3.71-3.60 (m, 4H, H-8', H-9', H-3", H-6"), 3.33 (appt d, J=9.4 Hz, 1H, H-4"), 2.24 (m, 2H, H-1'"), 2.17-1.88 (m, 9H, H-6', H-1'", H-2"', H-4"), 1.67 (s, 6H, H-7'"), 1.61 (s, 6H, H-8'"), 1.52 (m, 1H, H-6'), 1.37 (m, 2H, H-3"), 1.23 (m, 2H, H-3"), 0.96 (d, J=6.4 Hz, 6H, H-9'"); $^{13}$C NMR (126 MHz, MeOD) δ ppm 176.64, 176.02, (2C, —N—C=O aliphatic chain), 166.18 (C-4), 152.63 (C-2), 142.78 (C-6), 132.31, 132.26 (2C, C-6"), 125.57, 125.50 (2C, C-5'"), 103.05 (C-5), 101.59 (C-11'), 99.99 (C-1"), 89.82 (C-1'), 89.62 (C-4'), 75.55 (C-2'), 74.37 (C-5"), 73.11, 73.00 (2C, C-8', C-9'), 72.74 (C-4"), 72.48 (C-7'), 72.19 (C-3"), 70.86 (C-3'), 68.34 (C-5'), 63.23 (C-6"), 54.73 (C-2"), 54.36 (C-10'), 45.39, 44.91 (2C, C-1'"), 38.60, 38.50 (2C, C-3'"), 35.94 (C-6'), 31.78, 31.67 (2C, C-2'"), 26.66, 26.63 (2C, C-4"), 25.94

(C-7''), 19.65 (C-9''), 17.83 (C-8'''); IR (neat) ν: 3291 (O—H), 2966 (C—H), 2928 (C—H), 1700 (C=O), 1638 (C=O), 1541 (C=C), 1092 (C—N); LRMS m/z (ESI⁻): 915 [(M+FA-H)⁻, 100%]; HRMS m/z (ESI⁺): calc. $C_{41}H_{65}N_4O_{16}$ (M-H)⁻=869.4401, found 869.4407. (H-4'' signal in the 1H NMR spectrum observed to be partially overlapped by the solvent peak. Not all aliphatic signals in carbon spectrum were resolved. Characterisation was assisted by COSY, HSQC, and HMBC)

Di-N-heptanoyl tunicamycin (E2)

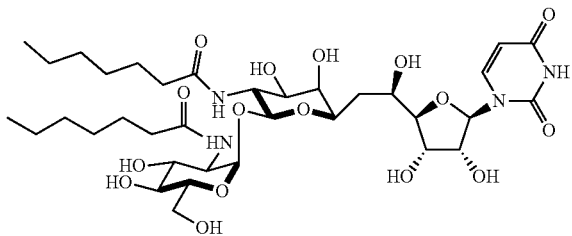

Heptanoic acid (5.5 μL, 0.039 mmol, 2.5 equiv) and DIC (6.1 μL, 0.039 mmol, 2.5 equiv) were added to DMF (0.25 mL) with the addition of TEA (2 μL) and DMAP (3.8 mg, 0.031 mmol, 2 equiv.) and stirred at room temperature for one hour. Then, α-D-glucosamine-(1''-11')-tunicamyl uracil dihydrochloride Compound D (10 mg, 0.016 mmol) was dissolved in DMF (0.25 mL) with the addition of TEA (4.1 μL), and added to the octanoic acid reaction mixture. TEA was added to final of 4 equivalents (6.7 μL total). The reaction mixture was stirred at room temperature. The reaction progress was checked by TLC (1/3/6, H₂O/iPrOH/EtOAc) and HPLC. The reaction was stopped after 18 hrs. The product was purified by HPLC, eluted at 12 min. The lyophilised product was washed with DCM and MilliQ water and resulted in 4.8 mg of the final product, 39% yield. $R_f$=0.4 (1/3/6, H₂O/iPrOH/EtOAc); $[\alpha]_D^{20}$=+26.8±0.7 (c 0.2, MeOH); Mp N/A; ¹H NMR (500 MHz, MeOD) δ ppm 7.92 (d, J=8.1 Hz, 1H, H-6), 5.93 (d, J=6.0 Hz, 1H, H-1'), 5.75 (d, J=8.1 Hz, 1H, H-5), 4.94 (d, J=3.4 Hz, 1H, H-1''), 4.61 (d, J=8.5 Hz, 1H, H-11'), 4.24-4.16 (m, 2H, H-2', H-3'), 4.06-3.99 (m, 2H, H-5', H-5''), 3.95 (dd, J=10.2, 8.6 Hz, 1H, H-10'), 3.90 (dd, J=10.6, 3.5 Hz, 1H, H-2''), 3.87-3.81 (m, 2H, H-4', H-6''), 3.77 (appt br d, J=9.1 Hz, 1H, H-7'), 3.71-3.62 (m, 4H, H-8', H-9', H-3'', H-6''), 3.34 (appt s, 1H, H-4''), 2.38-2.02 (m, 5H, 2×$CH_2^{fatty\ acyl}$, H-6'), 1.69-1.49 (m, 5H, 2×$CH_2^{fatty\ acyl}$, H-6'), 1.41-1.28 (m, 15H, $CH_2^{fatty\ acyl}$), 0.92 (t, J=6.8 Hz, 6H, $CH_3^{fatty\ acyl}$); ¹³C NMR (126 MHz, MeOD) δ ppm 177.18, 176.59, (2C, —N—C=O$^{fatty\ acyl}$), 166.17, (C-4), 152.64, (C-2), 142.77, (C-6), 103.06, (C-5), 101.28, (C-11'), 99.92, (C-1''), 89.77, (C-1'), 89.63, (C-4'), 75.53, (C-2'), 74.37, (C-5''), 73.04, (2C, C-8', C-9'), 72.61, (C-4''), 72.49, (C-7'), 72.11, (C-3''), 70.89, (C-3'), 68.34, (C-5'), 63.27, (C-6''), 54.76, (C-2''), 54.47, (C-10'), 37.81, 37.22, (2C, —COCH₂—$^{fatty\ acyl}$), 35.94, (C-6'), 32.87, 32.81, 30.26, 27.01, 26.82, 23.68, (6C, —CH₂—$^{fatty\ acyl}$), 14.44. (1C, —CH₃$^{fatty\ acyl}$); IR (neat) ν: 3305 (O—H), 2927 (C—H), 2856 (C—H), 1682 (C=O), 1645 (C=O), 1552 (C=C), 1467 (CH₂), 1376 (CH₃), 1259 (C—O), 1094 (C—N); LRMS m/z (ESI⁺): 813 [(M+Na)⁺, 100%]; HRMS m/z (ESI⁺): calc. $C_{35}H_{58}N_4O_{16}$ (M+Na)⁺=813.3740, found 813.3708.

Di-N-octanoyl-tunicamycin (E3)

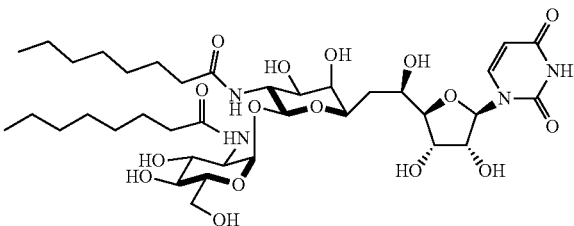

Octanoic acid (4.3 μL, 0.027 mmol, 2.5 equiv) and DIC (4.2 μL, 0.027 mmol, 2.5 equiv) were added to DMF (0.25 mL) with the addition of TEA (2 μL) and DMAP (2.7 mg, 0.022 mmol, 2 equiv.) and stirred at room temperature for one hour. Then, α-D-glucosamine-(1''-11')-tunicamyl uracil dihydrochloride Compound D (7 mg, 0.011 mmol) was dissolved in DMF (0.25 mL) with the addition of TEA (4.1 μL), and added to the octanoic acid reaction mixture. TEA was added to final of 4 equivalents. The reaction mixture was stirred at room temperature. The reaction progress was checked by TLC (1/3/6, H₂O/iPrOH/EtOAc) and HPLC. The reaction was stopped after 7 days. The product was purified by HPLC, eluted at 13.5 min. The lyophilised product was washed with DCM and MilliQ water and resulted in 2.5 mg of the final product, 28% yield. $R_f$=0.3 (1/3/6, H₂O/iPrOH/EtOAc); $[\alpha]_D^{20}$=+57.4±0.4 (c 0.2, MeOH); Mp N/A; ¹H NMR (500 MHz, MeOD) δ ppm 7.91 (d, J=8.1 Hz, 1H, H-6), 5.92 (d, J=6.0 Hz, 1H, H-1'), 5.75 (d, J=8.1 Hz, 1H, H-5), 4.94 (d, J=3.4 Hz, 1H, H-1''), 4.60 (d, J=8.5 Hz, 1H, H-11'), 4.24-4.15 (m, 2H, H-2', H-3'), 4.06-3.98 (m, 2H, H-5', H-5''), 3.95 (dd, J=10.0, 8.6 Hz, 1H, H-10'), 3.90 (dd, J=10.6, 3.4 Hz, 1H, H-2''), 3.87-3.80 (m, 2H, H-4', H-6''), 3.76 (dd, J=10.6, 1.6 Hz, 1H, H-7'), 3.70-3.61 (m, 4H, H-8', H-9', H-3'', H-6''), 3.34 (appt d, J=4.0 Hz, 1H, H-4''), 2.38-2.14 (m, 4H, 2×$CH_2^{fatty\ acyl}$), 2.10 (m, 1H, H-6'), 1.70-1.57 (m, 4H, 2×$CH_2^{fatty\ acyl}$), 1.53 (ddd, J=13.9, 11.4, 2.2 Hz, 1H, H-6'), 1.41-1.24 (appt br m, 16H, $CH_2^{fatty\ acyl}$), 0.91 (t, J=6.9 Hz, 6H, $CH_3^{fatty\ acyl}$); ¹³C NMR (126 MHz, MeOD) δ ppm 177.17, 176.58, (2C, —N—C=O$^{fatty\ acyl}$), 166.16 (C-4), 152.63 (C-2), 142.76 (C-6), 103.07 (C-5), 101.31 (C-11'), 99.95 (C-1''), 89.78 (C-1'), 89.63 (C-4'), 75.53 (C-2'), 74.37 (C-5''), 73.05 (2C, C-8', C-9'), 72.61 (C-4''), 72.49 (C-7'), 72.11 (C-3''), 70.90 (C-3'), 68.34 (C-5'), 63.27 (C-6''), 54.76 (C-2''), 54.47 (C-10'), 37.81, 37.21 (2C, —COCH₂—$^{fatty\ acyl}$), 35.94 (C-6'), 33.00, 32.97, 30.56, 30.33, 30.27, 27.05, 26.85, 23.75 (8C, —CH₂—$^{fatty\ acyl}$), 14.45 (2C, —CH₃$^{fatty\ acyl}$); IR (neat) ν: 3297 (O—H), 2957 (C—H), 2925 (C—H), 2853 (C—H), 1684 (C=O), 1644 (C=O), 1556 (C=C), 1469 (CH₂), 1258 (C—O), 1091 (C—N), 1016 (=C—H); LRMS m/z (ESI⁻): 931 [(M+TFA-H)⁻, 100%]; HRMS m/z (ESI⁺): calc. $C_{37}H_{62}N_4O_{16}Na$ (M+Na)⁺=841.4053, found 841.4045. (H-4'' signal in the 1H NMR spectrum observed to be partially overlapped by the solvent peak. Not all aliphatic signals in carbon spectrum were resolved. Characterisation was assisted by COSY and HSQC.)

Di-N-nonanoyl-tunicamycin (E4)

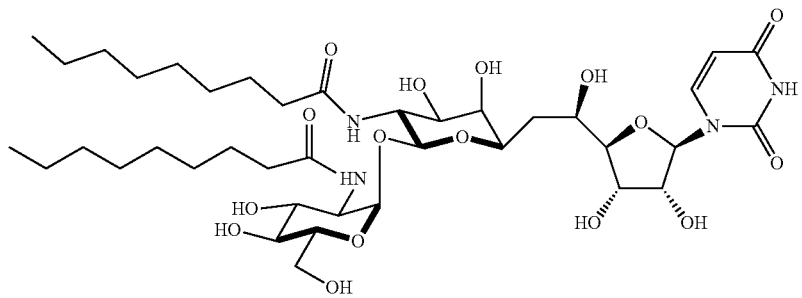

Nonanoic acid (6.8 μL, 0.039 mmol, 2.5 equiv) and DIC (6 μL, 0.039 mmol, 2.5 equiv) were added to DMF (0.25 mL) with the addition of TEA (2 μL) and DMAP (3.8 mg, 0.031 mmol, 2 equiv.) and stirred at room temperature for one hour. Then, α-D-glucosamine-(1″-11′)-tunicamyl uracil dihydrochloride Compound D (10 mg, 0.016 mmol) was dissolved in DMF (0.25 mL) with the addition of TEA (4.1 μL), and added to the octanoic acid reaction mixture. TEA was added to final of 4 equivalents (8.7 μL total). The reaction mixture was stirred at room temperature. The reaction progress was checked by TLC (1/3/6, H$_2$O/iPrOH/EtOAc) and HPLC. The reaction was stopped after 7 days. The product was purified by HPLC, eluted at 15 min. The lyophilised product was washed with DCM and MilliQ water and resulted in 3.4 mg of the final product, 26% yield.

$R_f$=0.4 (1/3/6, H$_2$O/iPrOH/EtOAc); [α]$_D^{20}$=+53.8±1.2 (c 0.3, MeOH); Mp N/A; $^1$H NMR (500 MHz, MeOD) δ ppm 7.93 (d, J=8.1 Hz, 1H, H-6), 5.95 (d, J=5.9 Hz, 1H, H-1′), 5.77 (d, J=8.1 Hz, 1H, H-5), 4.96 (d, J=3.0 Hz, 1H, H-1″), 4.62 (d, J=8.6 Hz, 1H, H-11′), 4.26-4.18 (m, 2H, H-2′, H-3′), 4.08-4.00 (m, 2H, H-5′, H-5″), 3.97 (t, J=9.1 Hz, 1H, H-10′), 3.92 (dd, J=10.7, 3.2 Hz, 1H, H-2″), 3.89-3.81 (m, 2H, H-4′, H-6″), 3.78 (appt br d, J=9.8 Hz, 1H, H-7′), 3.73-3.63 (m, 4H, H-8′, H-9′, H-3″, H-6″), 3.36 (appt d, J=4.2 Hz, 1H, H-4″), 2.41-2.16 (m, 4H, 2×CH$_2^{fatty\ acyl}$), 2.12 (appt br t, J=12.1 Hz, 1H, H-6′), 1.71-1.59 (m, J=6.7 Hz, 4H, 2×CH$_2^{fatty\ acyl}$), 1.55 (appt br t, J=12.6 Hz, 1H, H-6′), 1.34 (s, 20H, CH$_2^{fatty\ acyl}$), 0.93 (t, J=6.5 Hz, 6H, CH$_3^{fatty\ acyl}$); $^{13}$C NMR (126 MHz, MeOD) δ ppm 177.17, 176.58 (2C, —N—C═O$^{fatty\ acyl}$), 166.16 (C-4), 152.63 (C-2), 142.76 (C-6), 103.06 (C-5), 101.32 (C-11′), 99.97 (C-1″), 89.78 (C-1′), 89.62 (C-4′), 75.53 (C-2′), 74.37 (C-5″), 73.06, 73.04 (2C, C-8′, C-9′), 72.60 (C-4″), 72.49 (C-7′), 72.11 (C-3″), 70.89 (C-3′), 68.33 (C-5′), 63.27 (C-6″), 54.76 (C-2″), 54.46 (C-10′), 37.82, 37.21 (2C, —COCH$_2$—$^{fatty\ acyl}$), 35.94 (C-6′), 33.10, 33.09, 30.62, 30.58, 30.45, 30.43, 27.05, 26.85, 23.77 (9C, —CH$_2$—$^{fatty\ acyl}$), 14.47 (1C, —CH$_3^{fatty\ acyl}$); IR (neat) ν: 3301 (O—H), 2923 (C—H), 2852 (CH), 1738 (C═O), 1646 (C═O), 1544 (C═C), 1420 (CH$_2$), 1366 (CH$_3$), 1229 (C—O), 1092 (CN), 1015 (═C—H); LRMS m/z (ESI$^-$): 891 [(M+FA–H)$^-$, 100%]; HRMS m/z (ESI$^-$): calc. C$_{39}$H$_{65}$N$_4$O$_{16}$ (M–H)$^-$=845.4401, found 845.4412. (H-4″ signal in the 1H NMR spectrum observed to be partially overlapped by the solvent peak. Not all aliphatic signals in carbon spectrum were resolved. Characterisation was assisted by COSY and HSQC)

Di-N-decanoyl-tunicamycin (E5)

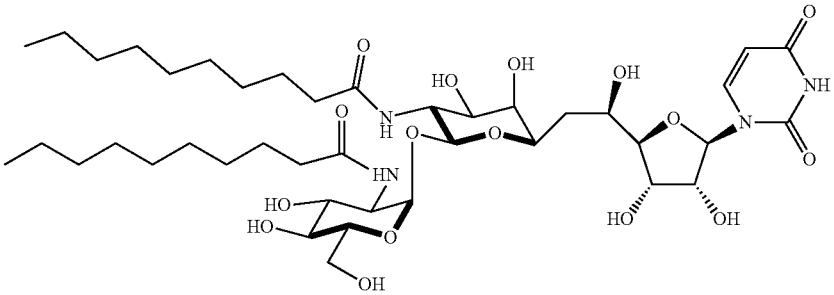

Decanoic acid (4.7 mg, 0.027 mmol, 2.5 equiv) and DIC (4.2 μL, 0.027 mmol, 2.5 equiv) were added to DMF (0.25 mL) with the addition of TEA (2 μL) and DMAP (2.7 mg, 0.022 mmol, 2 equiv.) and stirred at room temperature for one hour. Then, α-D-glucosamine-(1″-11′)-tunicamyl uracil dihydrochloride Compound D (7 mg, 0.011 mmol) was dissolved in DMF (0.25 mL) with the addition of TEA (4.1 μL), and added to the decanoic acid reaction mixture. TEA was added to final of 4 equivalents. The reaction mixture was stirred at room temperature and reaction progress was checked by TLC (1/3/6, H$_2$O/iPrOH/EtOAc) and HPLC. The reaction was stopped after 63 hours. The product was purified by HPLC, eluted at 16.5 min. The lyophilised product was washed with DCM and MilliQ water and resulted in 3 mg of the final product, 31% yield. $R_f$=0.4 (1/3/6, H$_2$O/iPrOH/EtOAc); [α]$_D$=+38.0±0.6 (c 0.3, MeOH); Mp N/A; $^1$H NMR (500 MHz, MeOD) δ ppm 7.91 (d, J=8.1 Hz, 1H, H-6), 5.92 (d, J=6.0 Hz, 1H, H-1′), 5.75 (d, J=8.1 Hz, 1H, H-5), 4.93 (d, J=3.4 Hz, 1H, H-1″), 4.59 (d, J=8.5 Hz, 1H, H-11'), 4.23-4.16 (m, 2H, H-2', H-3'), 3.97-3.92 (m, 2H, H-5', H-5''), 3.90 (appt t, J=8.5 Hz, 1H, H-10'), 3.84 (dd, J=10.6, 3.4 Hz, 1H, H-2''), 3.87-3.80 (m, 2H, H-4', H-6''), 3.76 (appt br dd, J=10.7, 1.7 Hz, 1H, H-7'), 3.71-3.61 (m, 4H, H-8', H-9', H-3'', H-6''), 3.33 (appt d, J=5.8 Hz, 1H, H-4''), 2.38-2.02 (m, 4H, 2×$CH_2^{fatty\ acyl}$), 2.10 (m, 1H, H-6'), 1.69-1.49 (m, 4H, 2×$CH_2^{fatty\ acyl}$), 1.55 (m, 1H, H-6'), 1.30 (s, 24H, $CH_2^{fatty\ acyl}$), 0.90 (t, J=6.9 Hz, 6H, $CH_3^{fatty\ acyl}$); $^{13}$C NMR (126 MHz, MeOD) δ ppm 177.17, 176.58 (2C, —NC=$O^{fatty\ acyl}$), 166.16 (C-4), 152.63 (C-2), 142.76 (C-6), 103.06 (C-5), 101.33 (C-11'), 100.00 (C-1''), 89.78 (C-1'), 89.62 (C-4'), 75.53 (C-2'), 74.37 (C-5''), 73.07, 73.04 (2C, C-8', C-9'), 72.60 (C-4''), 72.49 (C-7'), 72.11 (C-3''), 70.90 (C-3'), 68.33 (C-5'), 63.27 (C-6''), 54.76 (C-2''), 54.46 (C-10'), 37.82, 37.20 (2C, —$COCH_2$—$^{fatty\ acyl}$), 35.94 (C-6'), 33.12, 30.74, 30.72, 30.68, 30.63, 30.53, 27.05, 26.84, 23.78 (9C, —$CH_2$—$^{fatty\ acyl}$), 14.48 (2C, —$CH_3^{fatty\ acyl}$); IR (neat) ν: 3305 (O—H), 2922 (C—H), 2851 (C—H), 1683 (C=O), 1645 (C=O), 1551 (C=C), 1468 ($CH_2$), 1260 (C—O), 1094 (C—N), 1017 (=C—H); LRMS m/z (ESI$^-$): 919 [(M+FA–H)$^-$, 100%]; HRMS m/z (ESI$^+$): calc. $C_{41}H_{70}N_4O_{16}Na$ (M+Na)$^+$=897.4679, found 897.4666. (H-4'' signal in the 1H NMR spectrum observed to be partially overlapped by the solvent peak. Not all aliphatic signals in carbon spectrum were resolved. Characterisation was assisted by COSY and HSQC.)

Di-N-undecanoyl-tunicamycin (E6)

mixture was stirred at room temperature and reaction progress was checked by TLC (1/3/6, $H_2O$/iPrOH/EtOAc) and HPLC. The reaction was stopped after 68 hours. The product was purified by HPLC, eluted at 18 min. The lyophilised product was washed with DCM and MilliQ water and resulted in 3 mg of the final product, 30% yield. $R_f$=0.4 (1/3/6, $H_2O$/iPrOH/EtOAc); $[α]_D^{20}$=+30.9±0.4 (c 0.25, MeOH); Mp N/A; $^1$H NMR (500 MHz, MeOD) δ ppm 7.91 (d, J=8.1 Hz, 1H, H-6), 5.92 (d, J=6.0 Hz, 1H, H-1'), 5.75 (d, J=8.1 Hz, 1H, H-5), 4.93 (d, J=3.4 Hz, 1H, H-1''), 4.60 (d, J=8.5 Hz, 1H, H-11'), 4.23-4.15 (m, 2H, H-2', H-3'), 4.05-3.98 (m, 2H, H-5', H-5''), 3.95 (m, 1H, H-10'), 3.90 (dd, J=10.6, 3.4 Hz, 1H, H-2''), 3.86-3.80 (m, 2H, H-4', H-6''), 3.76 (appt br dd, J=10.7, 1.8 Hz, 1H, H-7'), 3.71-3.61 (m, 4H, H-8', H-9', H-3'', H-6''), 3.34 (m, 1H, H-4''), 2.37-2.14 (m, 4H, 2×$CH_2^{fatty\ acyl}$), 2.13-2.05 (m, 1H, H-6'), 1.68-1.56 (m, 4H, 2×$CH_2^{fatty\ acyl}$), 1.57-1.49 (m, 1H, H-6'), 1.30 (appt br s, 32H, $CH_2^{fatty\ acyl}$), 0.90 (t, J=6.9 Hz, 6H, $CH_3^{fatty\ acyl}$); $^{13}$C NMR (126 MHz, MeOD) δ ppm 177.17, 176.57, (2C, —N—C=$O^{fatty\ acyl}$), 166.22 (C-4), 152.67 (C-2), 142.76 (C-6), 103.06 (C-5), 101.34 (C-11'), 100.02 (C-1''), 89.78 (C-1'), 89.62 (C-4'), 75.53 (C-2'), 74.37 (C-5''), 73.07, 73.05 (2C, C-8', C-9'), 72.59 (C-4''), 72.49 (C-7'), 72.10 (C-3''), 70.90 (C-3'), 68.33 (C-5'), 63.27 (C-6''), 54.76 (C-2''), 54.46 (C-10'), 37.82, 37.20 (2C, —$COCH_2$—$^{fatty\ acyl}$), 35.94 (C-6'), 33.13, 30.82, 30.79, 30.77, 30.68, 30.64, 30.63, 30.54, 27.05, 26.83, 23.79 (11C, —$CH_2^{fatty\ acyl}$), 14.48 (2C, —$CH_3^{fatty\ acyl}$); IR (neat) ν: 3297 (O—H), 2956 (C—H), 2921 (C—H), 2852 (C—H), 1738 (C=O), 1719 (C=O),

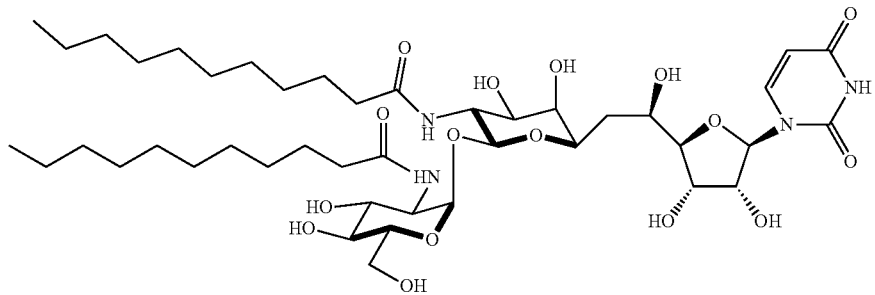

Undecanoic acid (5 mg, 0.027 mmol, 2.5 equiv) and DIC (4.2 μL, 0.027 mmol, 2.5 equiv) were added to DMF (0.25 mL) with the addition of TEA (2 μL) and DMAP (2.7 mg, 0.022 mmol, 2 equiv.) and stirred at room temperature for one hour. Then, α-D-glucosamine-(1''-11')-tunicamyl uracil dihydrochloride Compound D (7 mg, 0.011 mmol) was dissolved in DMF (0.25 mL) with the addition of TEA (4.1 μL), and added to the undecanoic acid reaction mixture. TEA was added to final of 4 equivalents. The reaction 1680 (C=C), 1645 (C=O), 1550 (N—H), 1468 ($CH_2$), 1366 ($CH_3$), 1229 (C—O—C), 1217 (C—OH), 1260 (C—O), 1092 (C—N), 1017 (=C—H); LRMS m/z (ESI$^-$): 947 [(M+FA–H)$^-$, 100%]; HRMS m/z (ESI$^+$): calc. $C_{43}H_{73}N_4O_{16}$ (M–H)$^-$=901.5027, found 901.5015. (H-4'' signal in the $^1$H NMR spectrum observed to be partially overlapped by the MeOD solvent peak. Not all aliphatic signals in carbon spectrum were resolved. Characterisation was assisted by COSY and HSQC.)

Di-N-dodecanoyl-tunicamycin (E7)

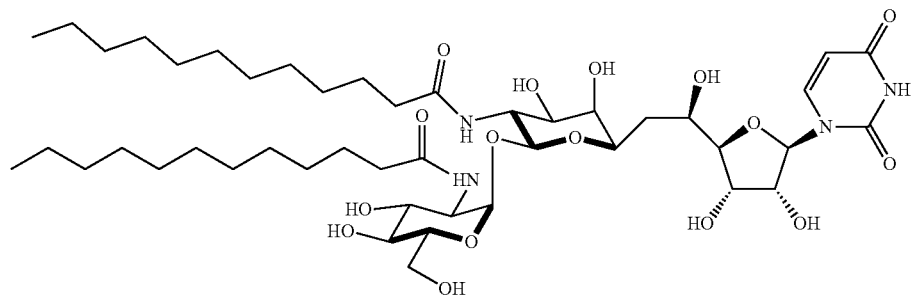

Dodecanoic acid (5.4 mg, 0.027 mmol, 2.5 equiv) and DIC (4.2 μL, 0.027 mmol, 2.5 equiv) were added to DMF (0.25 mL) with the addition of TEA (2 μL) and DMAP (2.7 mg, 0.022 mmol, 2 equiv.) and stirred at room temperature for one hour. Then, α-D-glucosamine-(1"-11')-tunicamyl uracil dihydrochloride Compound D (7 mg, 0.011 mmol) was dissolved in DMF (0.25 mL) with the addition of TEA (4.1 μL), and added to the dodecanoic acid reaction mixture. TEA was added to final of 4 equivalents. The reaction mixture was stirred at room temperature and reaction progress was checked by TLC (1/3/6, $H_2O$/iPrOH/EtOAc) and HPLC. The reaction was stopped after 68 hours. The product was purified by HPLC, eluted at 20.5 min. The lyophilised product was washed with DCM and MilliQ water and resulted in 3 mg of the final product, 29% yield. $R_f$=0.4 (1/3/6, $H_2O$/iPrOH/EtOAc); $[\alpha]_D^{20}$=+15.9±0.4 (c 0.25, MeOH); Mp N/A; $^1$H NMR (500 MHz, MeOD) δ 7.92 (d, J=8.1 Hz, 1H, H-6), 5.93 (d, J=5.9 Hz, 1H, H-1'), 5.76 (d, J=8.1 Hz, 1H, H-5), 4.94 (d, J=3.5 Hz, 1H, H-1"), 4.60 (d, J=8.5 Hz, 1H, H-11'), 4.24-4.17 (m, 2H, H-2', H-3'), 4.08-3.99 (m, 2H, H-5', H-5"), 3.96 (m, J=8.6 Hz, 1H, H-10'), 3.91 (dd, J=10.6, 3.4 Hz, 1H, H-2"), 3.88-3.80 (m, 2H, H-4', H-6"), 3.77 (appt br dd, J=11.1, 1.8 Hz, 1H, H-7'), 3.72-3.61 (m, 4H, H-8', H-9', H-3", H-6"), 2.39-2.15 (m, 4H, 2×$CH_2^{fatty\ acyl}$), 2.11 (m, 1H, H-6'), 1.70-1.57 (m, 4H, 2×$CH_2^{fatty\ acyl}$), 1.54 (m, 1H, H-6'), 1.40-1.28 (appt broad m, 32H, $CH_2^{fatty\ acyl}$), 0.91 (t, J=6.9 Hz, 6H, CH3 fatty acyl); $^{13}$C NMR (126 MHz, MeOD) δ ppm 177.17, 176.57 (2C, —N—C=$O^{fatty\ acyl}$), 166.16 (C-4), 152.63 (C-2), 142.76 (C-6), 103.06 (C-5), 101.35 (C-11'), 100.04 (C-1"), 89.77 (C-1'), 89.62 (C-4'), 75.52 (C-2'), 74.37 (C-5"), 73.08, 73.04 (2C, C-8', C-9'), 72.60 (C-4"), 72.49 (C-7'), 72.10 (C-3"), 70.90 (C-3'), 68.33 (C-5'), 63.27 (C-6"), 54.76 (C-2"), 54.45 (C-10'), 37.82, 37.19 (2C, —$COCH_2$—$^{fatty\ acyl}$), 35.94 (C-6'), 30.87, 30.83, 30.79, 30.77, 30.68, 30.65, 30.63, 30.55, 27.05, 26.83, 23.79 (11C, —$CH_2$—$^{fatty\ acyl}$), 14.48 (2C, —$CH_3^{fatty\ acyl}$); IR (neat) ν: 3297 (O—H), 2956 (C—H), 2921 (C—H), 2851 (C—H), 1682 (C=O), 1646 (C=O), 1556 (C=C), 1468 ($CH_2$), 1260 (C—O), 1092 (C—N), 1016 (=C—H); LRMS m/z (ESI$^-$): 976 [(M+FA–H)$^-$, 100%]; HRMS m/z (ESI$^+$): calc. $C_{45}H_{78}N_4O_{16}Na$ (M+Na)$^+$=953.5305, found 953.5334. (H-4" signal in the 1H NMR spectrum observed to be partially overlapped by the solvent peak. Not all aliphatic signals in carbon spectrum were resolved. Characterisation was assisted by COSY and HSQC)

General Procedure

The general procedure given below was used for the synthesis of compounds of formula E (as shown in the schemes at the beginning of this Example, Example 1).

A 0.022 M solution of NaOMe in MeOH was prepared by dissolving sodium (4.1 mg, 0.177 mmol) in anhydrous MeOH (8 mL). The resulting NaOMe solution was then added to Tri-N-(tert-butoxylcarbonyl)-octa-O-acetyl-tunicamycin 5 (260 mg, 0.177 mmol) in a 25 mL round-bottomed flask and the resulting orange solution stirred for 4 h under argon. The reaction mixture was diluted with MeOH (5 mL) and carefully quenched with DOWEX 50 W×8 ft form resin. The resin was removed by filtration and the filtrate concentrated in vacuo. The resulting yellow solid was washed with $Et_2O$ (2×2 mL) to remove hydrolyzed lipids and dried under an argon stream. The resulting light-yellow solid was dissolved in TFA (4 mL) and stirred at ambient temperature for 1 h. The reaction mixture was then concentrated in vacuo and azeotroped with toluene (2×4 mL). The resulting solid was washed with $Et_2O$ (5 mL) and dried under an argon stream to yield crude diamine as an off-white solid. In a separate flask, the carboxylic acid (0.372 mmol) and HATU (141 mg, 0.372 mmol) were dissolved in dry DMF (2 mL) and cooled to 0° C. DIPEA (123 uL, 0.708 mmol) was added and the resulting yellow solution stirred at 0° C. for 15 min. A solution of the crude diamine in DMF (2 mL) was added and the resulting yellow solution stirred at ambient temperature for 16-22 h. The reaction mixture was concentrated in vacuo and redissolved in 1:1:1 MeCN:$H_2O$:$^i$PrOH (6 mL) and purified by RP-HPLC: Column=Phenomenex Synergi 4u Fusion hydro-RP 80a; flow rate=12 mL/min; detection=254 nm; solvent A=0.1% formic acid in $H_2O$ and solvent B=0.1% formic acid in MeCN; gradient=30% B (2 min), 30-80% B (10 min), 80-98% B (1 min), 98% B (5 min), 98-30% B (1 min), 30% B (5 min). Product containing fractions were pooled, concentrated, frozen and lyophilized to yield the compounds E. Compounds E3 and E4 were prepared by this method in respective yields of 22% and 19% over three steps.

Preparation of Biocompatible Formulation for In Vivo Testing

To prepare a biocompatible formulation for in vivo testing, Compounds E3 and E4 can be dissolved in concentrations >10 mg/mL in an aqueous solution of Tween 80 (0.5%) and sodium hydroxide (0.1-0.5%).

Example 2: Bioactivity of Lipid Altered Tunicamycin Analogues and Underlying Scaffolds Against *Bacillus subtilis* (EC1524) and *Bacillus cereus* (ATCC11778)

Underlying scaffolds A, B, C and D and lipid-altered analogues E1 to E7 were assayed for potency against *Bacillus subtilis* (EC1524) and *Bacillus cereus* (ATCC11778). Naturally extracted tunicamycin (TM) was also assayed as a control.

Bioactivity was assessed using the Kirby-Bauer disc diffusion susceptibility test. Oxoid Blank Discs were impregnated with the desired test substance. A 0.5 McFarland standard inoculum was prepared by adding 3-5 single colonies to 10 mL MH broth in a 15 mL falcon tube and standardised to 0.5 McFarland standard. The inoculum was used within 10 minutes. A sterile cotton swab was dipped in the inoculum, gently pressed against the side of the tube to remove excess liquid, and generously streaked on MH agar plate to fully cover the plate. The impregnated disc was carefully placed on the agar. The plate was incubated at 35° C. for 20 hrs overnight. A digital calliper was used to measure the zone diameter. The recorded zone diameter is an average of three zone diameters measured of one zone.

Each 6 mm disc was impregnated with 5 µg of the relevant compound (TM, A, B, C, D, or any of E1 to E7), and the diffusion zone recorded after 20 hours.

FIG. 1 shows results of the Kirby-Bauer disc diffusion susceptibility test conducted using *Bacillus subtilis* as a test organism. FIG. 1 and Table 1 below shows result obtained for E2 to E7 and TM. Non-lipidated scaffolds A, B, C and D were completely inactive against *Bacillus subtilis*. FIG. 1 and Table 1 also shows analogous results obtained using *Bacillus cereus* as a test organism. Results are shown for E2 to E7 and TM. The activities of the tested substances against *Bacillus subtilis* and *Bacillus cereus* are shown in Table 1. Values quoted are zone diameters, with larger numbers indicating higher antibacterial activity. Non-lipidated scaffolds A, B, C and D were completely inactive against *Bacillus cereus*. With both organisms *Bacillus cereus* and *Bacillus subtilis*, the most active lipid altered tunicamycin analogues displayed essentially identical antibacterial activity to natural tunicamycin (TM).

TABLE 1

| | Reference in | Diffusion distance (mm) | |
|---|---|---|---|
| Substance | FIG. 1 | *Bacillus subtilis* | *Bacillus cereus* |
| TM | TM | 15 | 13 |
| E2 | 3 | 10 | |
| E3 | 4 | 16 | 12 |
| E4 | 5 | 16 | 13 |
| E5 | 6 | 10 | 9 |
| E6 | 7 | 6 | 7 |
| E7 | 8 | | |

Minimal and half maximal inhibitory concentrations (MIC and IC50 values) and minimal bactericidal concentration (MBC) of TM and the lipid modified tunicamycin analogues E1 to E7 were assayed against *Bacillus subtilis* and *Bacillus cereus*.

In a sterile 96-well plate, serial dilutions were made with the test substance to final volume of 50 μL. Inoculum was then prepared in Mueller-Hinton broth to 0.5 McFarland and diluted before adding 50 μL to the well to make $1\times10^5$ CFU/mL. The culture plate was incubated at 35° C. for 20-24 hours. A positive growth control and sterility wells were also prepared along with the culture wells. Absorbance at $OD_{600}$ was taken using BMG Labtech SPECTROstar Omega spectrophotometer. MIC was determined by the lowest concentration without growth. IC50 was determined from plotting a dose-response curve. Data were analysed using Graph Pad PRISM 5.01 software. Dose-response curves were plotted from three independent data sets with SEM error bars. To determine the MBC, using a multichannel pipette, 1 μL of culture broth was taken from the same 96-well microdilution growth plate and carefully inoculated on surface of MH agar plate. The plate is then incubated for additional 20 hours at 35° C. The MBC value is the lowest concentration without observed growth on the agar. Results are shown in Table 2.

TABLE 2

| | *Bacillus subtilis* | | | *Bacillus cereus* | | |
|---|---|---|---|---|---|---|
| Substance | MIC (μg/mL) | MBC (μg/mL) | IC50 (μg/mL) | MIC (μg/mL) | MBC (μg/mL) | IC50 (μg/mL) |
| TM | 0.0015 | >0.0015 | 0.001484 | 0.195 | 25 | 0.003163 |
| E1 | 6.25 | >100 | 0.415 | 100 | >200 | 6.292 |
| E2 | 6.25 | >50 | 3.39 | 100 | >200 | 13.33 |
| E3 | 0.78 | >0.98 | 0.20114 | 6.25 | 50 | 0.7823 |
| E4 | 0.024 | >0.06 | 0.01457 | 0.78 | 25 | 0.07229 |
| E5 | 0.39 | >0.39 | 0.1141 | 0.39 | 12.5 | 0.0461 |
| E6 | 1.56 | >6.25 | 0.8519 | 0.78 | 25 | 0.08781 |
| E7 | 100 | >200 | 58.87 | 50 | >200 | 1.402 |

Example 3: Bioactivity of Lipid Altered Tunicamycin Analogues and Underlying Scaffolds Against *Pseudomonas aeruginosa* (ATCC27853)

Underlying scaffolds A, B, C and D and lipid-varied analogues E1 to E7 were assayed for potency against *Pseudomonas aeruginosa* (ATCC27853), according to the methods of Example 2. Results of the Kirby-Bauer disc diffusion susceptibility test conducted using *Pseudomonas aeruginosa* (ATCC27853) as a test organism are shown in FIG. 2 and in Table 3. MIC, MBC and IC50 values were also obtained as in Example 2. Results are shown in Table 3.

TABLE 3

| | | *Pseudomonas aeruginosa* | | | |
|---|---|---|---|---|---|
| Substance | Reference in FIG. 2 | Diffusion distance (mm) | MIC (μg/mL) | MBC (μg/mL) | IC50 (μg/mL) |
| TM | TM | | >400 | >400 | >400 |
| E1 | | | 200 | >400 | 70.29 |
| E2 | 3 | 7 | 100 | >400 | 62.44 |
| E3 | 4 | 9 | 100 | >400 | 46.54 |
| E4 | 5 | 13 | 100 | 400 | 54.98 |
| E5 | 6 | 12 | 100 | 400 | 53.46 |
| E6 | 7 | 12 | 100 | 400 | 63.17 |
| E7 | 8 | 8 | 200 | >400 | 81.94 |

Inhibitory activity against *Pseudomonas aeruginosa* was observed for E4 to E6. Surprisingly, this inhibitory activity was greater than that observed for natural tunicamycin.

Example 4: Bioactivity of Lipid Altered Tunicamycin Analogues and Underlying Scaffolds Against *Mycobacterium tuberculosis* H37RV One of the most pernicious Gram-positive pathogens is *Mycobacterium tuberculosis*. It is responsible for 1.3 million deaths per annum and it is estimated that a third of the world's population is infected. It is also resistant to common antibacterial treatments.

TM and the lipid-varied analogues E1 to E7 were assayed for potency against *Mycobacterium tuberculosis* H37RV. MIC values were determined as in Example 2, except that MIC values were determined in GAST/Fe growth medium and in 7H9/ADC/Tw (ADC=Albumin dextrose complex; Tw=Tween) growth medium, and were assessed at 1 and 2 weeks. Results are shown in Table 4.

TABLE 4

| Substance | 1-week MIC (μg/mL) | | 2-week MIC (μg/mL) | |
|---|---|---|---|---|
| | 7H9/ADC/Tw | GAST/Fe | 7H9/ADC/Tw | GAST/Fe |
| Water | No inhibition | No inhibition | No inhibition | No inhibition |
| Methanol | No inhibition | No inhibition | No inhibition | No inhibition |
| TM | 0.7 | 0.12 | 0.9 | 0.18 |
| E1 | 22.5 | 5.6 | 22.5 | 11.2 |
| E2 | 7.5 | 2.8 | 7.5 | 2.8 |
| E3 | 0.94 | 0.23 | 1.4 | 0.35 |
| E4 | 0.23 | 0.029 | 0.35 | 0.04 |
| E5 | 1.4 | 0.18 | 1.4 | 0.35 |
| E6 | 5.6 | 2.8 | 5.6 | 2.8 |
| E7 | 22.5 | 11.2 | 30 | 11.2 |

Surprisingly, the MIC values for lipid-altered tunicamycin analogue E4 are significantly lower, in some cases approximately 5-fold lower than naturally occurring tunicamycin TM. This signifies that the lipid-altered tunicamycin analogue E4 is more potent than TM. Furthermore, these values are comparable with current first line drugs such as Isoniazid (for which MIC=0.1 in 7H9 growth medium) and Rifampicin (MIC=0.125-0.25 in 7H9 growth medium).

Example 5: Determination of Cytotoxicity of Lipid Altered Tunicamycin Analogues and Underlying Scaffolds in Human Liver Cells and in Human Kidney Cells Underlying scaffolds A, B, C and D and lipid-varied analogues E1 to E7 were assayed for cytotoxicity towards human liver cells (Hep2G) and human kidney cells (HEK293). Following administration of the relevant compound (A, B, C, D, or any of E1 to E7), cells were examined both by analysis of the resulting proliferation dose response curve and by analysis of any morphological changes by microscopy.

HepG2 and HEK293 Cell Culture.

Mammalian cells were cultured in DMEM medium supplemented with 10% heat inactivated fetal bovine serum (FBS, v/v). The cultures were maintained in a humidified incubator at 37° C. in 5% $CO_2$/95% air. FBS was reduced to 2% for the cell proliferation assay.

Cell Proliferation Assay

In sterile 96-well plate, each well was seeded with $1\times10^5$ cells. The cells were then grown confluent overnight in 100 μL DMEM with 10% FBS. The medium was replenished with DMEM with 2% FBS and added vehicle control or test substance the next day. For test substance in methanol, stock was added to 25 μL of DMEM with 2% FBS or PBS and placed in a laminar flow hood to let the methanol evaporate (about 1-3 hrs). Once the methanol has evaporated, DMEM with 2% FBS was added to final volume of 100 μL of desired test concentration. A blank methanol control was also made to ensure any cytotoxicity does not result from methanol contamination. Cells were grown for additional 24 hrs. The cell viability was determined by using a Promega CellTiter 96 AQueous One Solution Cell Proliferation Assay System following the manufacturer's protocol.

Incubation of the cells with TM over a period of 24 hours showed both clear cytotoxicity (FIG. 3) and morphological changes (FIG. 4). A dose response curve for TM is shown in FIG. 3. Specifically, half lethal dose values ($LD_{50}$) for TM were 42.55±4.45 μg/mL towards HepG2 liver cells and 71.92±24.84 μg/mL towards HEK293 kidney cells. Over longer time periods, cell stress responses were observed that also distorted proliferation assays.

In contrast to the results obtained with TM, the scaffolds (A to D) and the lipidated variants E1 to E7 displayed no significant toxicity towards HepG2 liver cells or HEK293 kidney cells. No dose response curve is shown for A to D or E1 to E7 due to the low cytotoxicity of these compounds. Surprisingly, at doses as high as 400 μg/mL, minimal cytotoxicity was observed. Higher concentrations resulted in precipitation of tunicamycin and lipid variants E1 to E7. Even more surprisingly, incubation of HepG2 liver cells and HEK293 kidney cells for 24 hours with 400 μg/mL E1 to E7 led to a high level (>75%) of viable cells exhibiting no morphological changes.

Minimum lethal dosages for TM and E1 to E7 are therefore as shown in Table 5.

TABLE 5

| | Minimum lethal dose/μg/mL | |
|---|---|---|
| Substance | HepG2 | HEK293 |
| TM | 100 | 100 |
| E1 | >400 | >400 |
| E2 | >400 | >400 |
| E3 | >400 | >400 |
| E4 | >400 | >400 |
| E5 | >400 | >400 |
| E6 | >400 | >400 |
| E7 | >400 | >400 |

Example 6: Determination of the Relative Therapeutic Index of Lipid Altered Tunicamycin Analogues Using *Bacillus subtilis* (EC1524), *Bacillus cereus* (ATCC11778), and *Mycobacterium tuberculosis* H37RV The Relative Therapeutic Index (RTI) was determined. RTI is the ratio between the minimal lethal dose calculated in Example 5 and the minimal inhibition concentration (determined in Examples 2 to 4). The microdilution broth test and cytotoxicity test were carried out by serial 2-fold dilutions. In cases when no cytotoxicity was detectable at 400 μg/mL, a minimal lethal dose of 800 μg/mL was used to calculate the RTI. Results are shown in Table 6.

TABLE 6

| | RTI | | | |
|---|---|---|---|---|
| Substance | *B. subtilis* | *B. cereus* | *M. tuberculosis* (2 weeks in 7H9/ADC/Tw) | *M. tuberculosis* (2 weeks in GAST/Fe) |
| TM | 66667 | 513 | 111 | 556 |
| D | 8 | 8 | 13 | 13 |
| E1 | 128 | 8 | 36 | 71 |
| E2 | 128 | 8 | 107 | 286 |
| E3 | 1026 | 128 | 571 | 2286 |
| E4 | 33333 | 1026 | 2286 | 20000 |
| E5 | 2051 | 2051 | 571 | 2286 |
| E6 | 513 | 1026 | 143 | 286 |
| E7 | 8 | 16 | 27 | 71 |

Example 7: Pharmacokinetic/Pharmacodynamics (PK/PD) Studies on Intraperitoneal (IP) Injections After extensive solubility testing a suitable formulation was found for the tunicamycin analogues. The formulation includes 90% phosphate-buffer-saline (PBS) at pH=7.3, 10% ethanol, with 1% Tween-80 surfactant added to the final mixture. This formulation is suitable for solubility of up to 1.5 mg/mL of the compounds.

Figure 5:
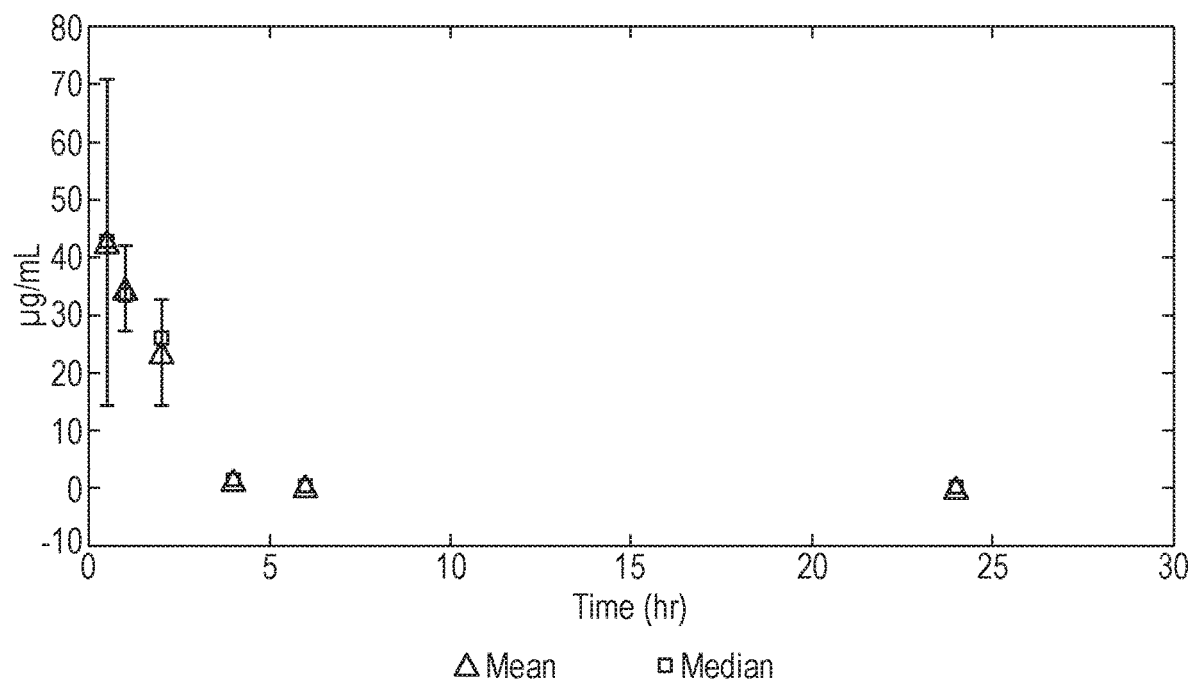
FIG. 5 shows a pharmacokinetic curve for di-N-octanoyl-tunicamycin (also referred to as compound E3 or TM-8) after intraperitoneal injection in sixteen mice. The initial dose was 30 mg/kg. The x-axis indicates the time in hours after the initial injection and the y-axis indicates the blood plasma concentration of TM-8 in μg/mL in the mice.

A single-dose PK study was done using 16 mice at a dose of 30 mg/kg for the TM-8 analogue, di-N-octanoyl-tunicamycin. This gave the PK curve shown in FIG. 5. The compound was easily detectable 6 hours after the injection, with some detectability. This study confirmed that the formulation was suitable for injections, and the drug is stable enough in physiological conditions.

The invention claimed is:

1. An oligosaccharide which is a compound according to Formula (I), or a pharmaceutically acceptable salt thereof,

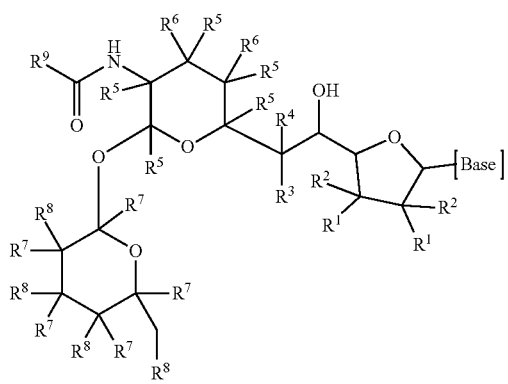

[FORMULA (I)]

wherein:
- [Base] is a natural nucleobase selected from adenine, cytosine, guanine, thymine and uracil;
- each $R^1$, which may be the same or different, is independently H, OH, —OPO(OH)$_2$, or halogen;
- each $R^2$, which may be the same or different, is independently H, halogen, or $C_1$ to $C_2$ alkyl;
- $R^3$ and $R^4$, which may be the same or different, are each independently H, OH, halogen, $C_1$ to $C_2$ alkyl, $C_1$ to $C_2$ alkoxy, or —NR$^{10}$R$^{11}$;
- each $R^5$, which may be the same or different, is independently H, halogen, or $C_1$ to $C_2$ alkyl;
- each $R^6$, which may be the same or different, is independently OH, halogen, —OPO(OH)$_2$, —OCO$_2$CH$_3$, —NHCOCH$_3$ or $C_1$ to $C_2$ alkoxy;
- one or more $R^7$ and/or one or more $R^8$ is a group —NHC(O)R$^9$; the remaining groups $R^7$, which may be the same or different, are independently H, halogen, or $C_1$ to $C_2$ alkyl; and the remaining groups $R^8$, which may be the same or different, are independently OH, halogen, —OPO(OH)$_2$, —OCO$_2$CH$_3$, —NHCOCH$_3$ or $C_1$ to $C_2$ alkoxy;
- each $R^9$, which may be the same or different, is independently $C_3$ to $C_{20}$ alkyl, $C_3$ to $C_{20}$ alkenyl, or $C_3$ to $C_{20}$ alkynyl, wherein $R^9$ may be unsubstituted or may be substituted by from 1 to 6 substituents selected from halogen, OH, $C_1$ to $C_4$ alkoxy and —NR$^{10}$R$^{11}$; and
- each $R^{10}$ and $R^{11}$, which may be the same or different, is independently H or $C_1$ to $C_4$ alkyl.

2. An oligosaccharide according to claim 1 which is a compound according to Formula (II), or a pharmaceutically acceptable salt thereof

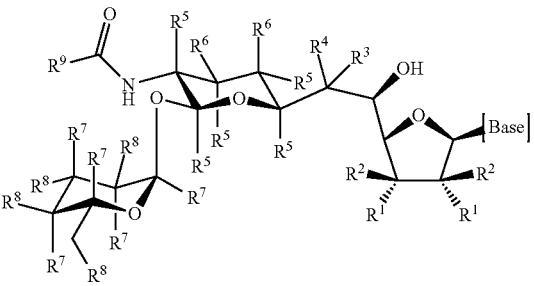

[FORMULA (II)]

wherein $R^1$ to $R^{11}$ and [Base] are as defined in claim 1.

3. An oligosaccharide according to claim 1 wherein [Base] is thymine or uracil.

4. An oligosaccharide according to claim 1 wherein each $R^1$, which may be the same or different, is independently OH or —OPO(OH)$_2$.

5. An oligosaccharide according to claim 1 wherein each $R^2$, which may be the same or different, is independently H or methyl.

6. An oligosaccharide according to claim 1 wherein $R^3$ and $R^4$ are each H.

7. An oligosaccharide according to claim 1 wherein each $R^5$, which may be the same or different, is independently H or $C_1$ to $C_2$ alkyl.

8. An oligosaccharide according to claim 1 wherein each $R^6$, which may be the same or different, is independently OH, —NHCOCH$_3$ or —OPO(OH)$_2$.

9. An oligosaccharide according to claim 1 wherein one of the $R^7$ and/or $R^8$ groups which are —NHC(O)R$^9$ is bonded to the C2" carbon.

10. An oligosaccharide according to claim 1 wherein the total number of $R^7$ and $R^8$ groups which are —NHC(O)R$^9$ is from 1 to 3; the remaining groups $R^7$, which may be the same or different, are independently H or $C_1$ to $C_2$ alkyl, and the remaining groups $R^8$, which may be the same or different, are independently OH, —NHCOCH$_3$ or —OPO(OH)$_2$.

11. An oligosaccharide according to claim 10 wherein one group $R^8$ is —NHC(O)R$^9$; the groups $R^7$, which may be the same or different, are independently H or $C_1$ to $C_2$ alkyl; and the remaining groups $R^8$, which may be the same or different, are independently OH, —NHCOCH$_3$ or —OPO(OH)$_2$, according to Formula (IV)

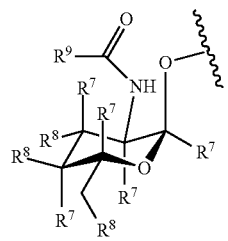

[FORMULA (IV)]

12. An oligosaccharide according to claim 1 wherein each $R^9$, which may be the same or different, is independently $C_4$ to $C_{16}$ alkyl, or $C_4$ to $C_{16}$ alkenyl, wherein $R^9$ is unsubstituted or substituted by from 1 to 4 substituents selected from halogen, OH, $C_1$ to $C_4$ alkoxy, and —NR$^{10}$R$^{11}$.

13. An oligosaccharide according to claim 1 wherein each $R^9$, which may be the same or different, is independently an unsubstituted $C_7$ to $C_9$ alkyl group.

14. An oligosaccharide according to claim 1 having a structure according to Formula (III)

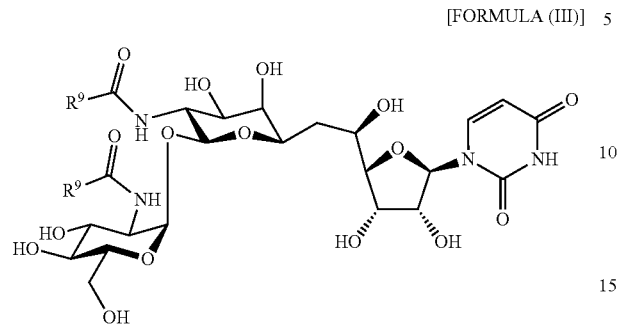

[FORMULA (III)]

wherein each $R^9$, which may be the same or different, is independently $C_3$ to $C_{20}$ alkyl, $C_3$ to $C_{20}$ alkenyl or $C_3$ to $C_{20}$ alkynyl, wherein $R^9$ may be unsubstituted or may be substituted by from 1 to 6 substituents selected from Mogen, OH, $C_1$ to $C_4$ alkoxy and $-NR^{10}R^{11}$; and each $R^{10}$ and $R^{11}$, which may be the same or different, is independently H or $C_1$ to $C_4$ alkyl.

15. An oligosaccharide according to claim 14 wherein $R^9$ is selected from

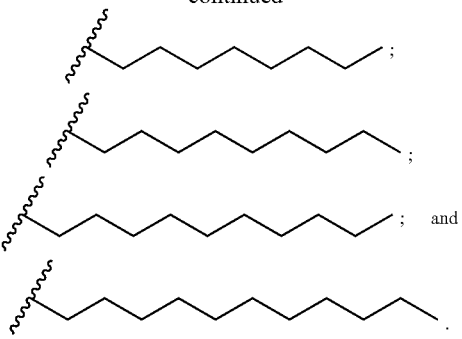

16. A pharmaceutical composition comprising an oligosaccharide according to claim 1 and a pharmaceutically acceptable carrier or diluent.

17. A method of treating a subject suffering from or susceptible to a bacterial infection, which method comprises administering an effective amount of an oligosaccharide according to claim 1, or a pharmaceutical composition comprising an oligosaccharide according to claim 1 and a pharmaceutically acceptable carrier or diluent, to said subject.

18. The method according to claim 17, wherein the bacterial infection is caused by *Bacillus, Pseudomonas, Mycobacterium, Staphylococcus*, or *Escherichia*.

19. The method according to claim 18, wherein the bacterial infection is caused by *Mycobacterium tuberculosis*.

20. The method according to claim 17, wherein the oligosaccharide or pharmaceutical composition is for use in treating or preventing tuberculosis.

\* \* \* \* \*